(12) United States Patent
Tyagi et al.

(10) Patent No.: US 12,162,983 B2
(45) Date of Patent: Dec. 10, 2024

(54) PRODUCTION OF POLYHYDROXYALCANOATES FROM PULP AND PAPER WASTE STREAMS

(71) Applicant: INSTITUT NATIONAL DE LA RECHERCHE SCIENTIFIQUE, Quebec (CA)

(72) Inventors: Rajeshwar Dayal Tyagi, Quebec (CA); Rajwinder Kaur, Kapurthala (IN)

(*) Notice: Subject to any disclaimer, the term of this patent is extended or adjusted under 35 U.S.C. 154(b) by 619 days.

(21) Appl. No.: 17/413,801

(22) PCT Filed: Dec. 12, 2019

(86) PCT No.: PCT/CA2019/051797
§ 371 (c)(1),
(2) Date: Jun. 14, 2021

(87) PCT Pub. No.: WO2020/118439
PCT Pub. Date: Jun. 18, 2020

(65) Prior Publication Data
US 2022/0017692 A1    Jan. 20, 2022

Related U.S. Application Data

(60) Provisional application No. 62/778,349, filed on Dec. 12, 2018.

(51) Int. Cl.
| | |
|---|---|
| C08G 63/78 | (2006.01) |
| C08G 63/06 | (2006.01) |
| C08H 8/00 | (2010.01) |
| C08J 11/10 | (2006.01) |

(52) U.S. Cl.
CPC ............ *C08G 63/78* (2013.01); *C08G 63/06* (2013.01); *C08H 8/00* (2013.01); *C08J 11/10* (2013.01)

(58) Field of Classification Search
USPC ........................................................ 521/40
See application file for complete search history.

(56) References Cited

FOREIGN PATENT DOCUMENTS

WO PCT/CA2019/051797    12/2019

OTHER PUBLICATIONS

Bhuwal et al., "Isolation and Screening of Polyhydroxyalkanoates Producing . . . ", International Journal of Biomaterials, May 26, 2013, vol. 2013, Article ID 752821.
Kucera et al., "Production of Polyhydroxyalkanoates Using Hydrolyzaes of Spruce . . . ", Bioengineering, May 28, 2017, vol. 4, pp. 1/9-9/9.
Mengmeng, et al., "Optimal Production of Polyhydroxyalkanoates (PHA) in Activated . . . ", www.elsevier.com/locate/biortech, Oct. 21, 2008.
Saraale, et al., "Characterization of Poly-3-Hydroxybutyrate (PHB) Produced . . . ", International Journal of Biological Macromolecules, Jul. 20, 2015.
Pan et al., "Production of Polyhydroxyalkanoates by Burkholderia . . . ", J Ind Microbiol Biotechnol, Sep. 28, 2011, vol. 39, pp. 459-469.
Yan et al., "Bioplastics from Waste Activaed Sludge-Batch Process", Practice of Periodical of Hazardous Toxic and Radioactive Waste Management, Oct. 2008.
Yan et.al., "Polyhydroxyalkanoates (PHA) production using wastewater as a carbon source . . . ", 2006, Water Science and Technology, vol. 53, No. 6, pp. 175-180.
Llano et.al., "Detoxification of a Lignocellulosis Waste from a Pulp Mill to Enhance Its Fermentation Prospects . . . ", Mar. 11, 2017, Energies, 2017, 10, pp. 1-18.
Kumar et.al., "Municipal secondary sludge as carbon source for production and characterization . . . ", Bioresource Technology Reports, Sep. 27, 2018, vol. 4, p. 106-113.
Chairattanamanokorn et.al., "Additional Paper Waste in Pulping Sludge for Biohydrogen . . . ", Applied Chemistry and Biotechnology, Nov. 19, 2011, vol. 166, p. 389-401.

*Primary Examiner* — Terressa Boykin
(74) *Attorney, Agent, or Firm* — J. Wiley Horton

(57) ABSTRACT

A process for producing polyhydroxyalkanoates (PHA) is provided. The process comprises: providing a waste stream comprising lignocellulosic materials; adding an calcium-containing mineral to the waste stream; heat-treating the waste stream in the presence of the calcium-containing mineral, to obtain a treated waste stream; fermenting at least one strain of PHA-producing microorganism in a culture medium comprising the treated waste stream as a carbon source, to produce the PHA; and extracting the PHA from the PHA-producing microorganism.

20 Claims, 10 Drawing Sheets

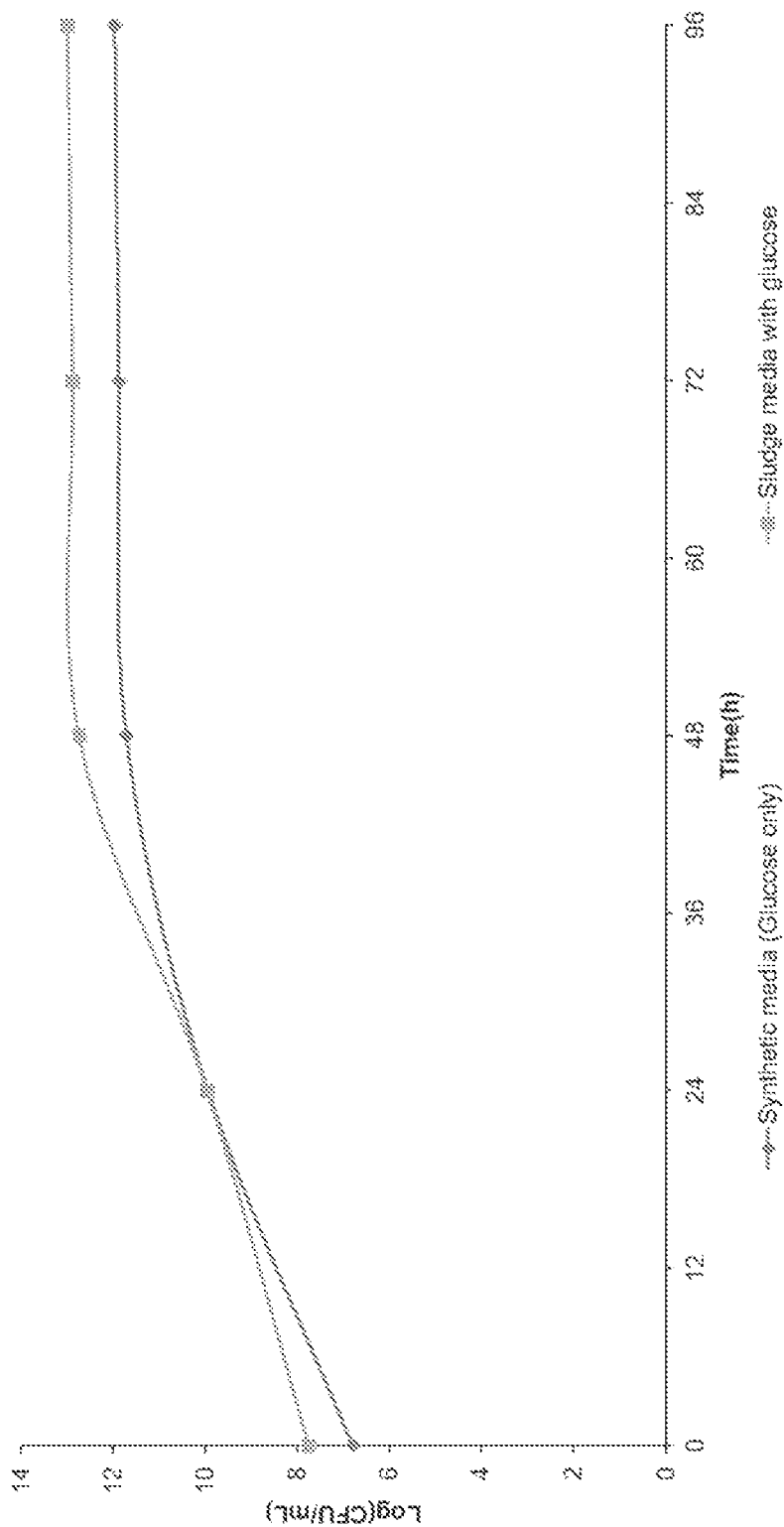
FIGURE 5. Comparison of PHA producing microorganism growth trend using synthetic media and sludge media incorporated synthetic media (fortified with glucose)

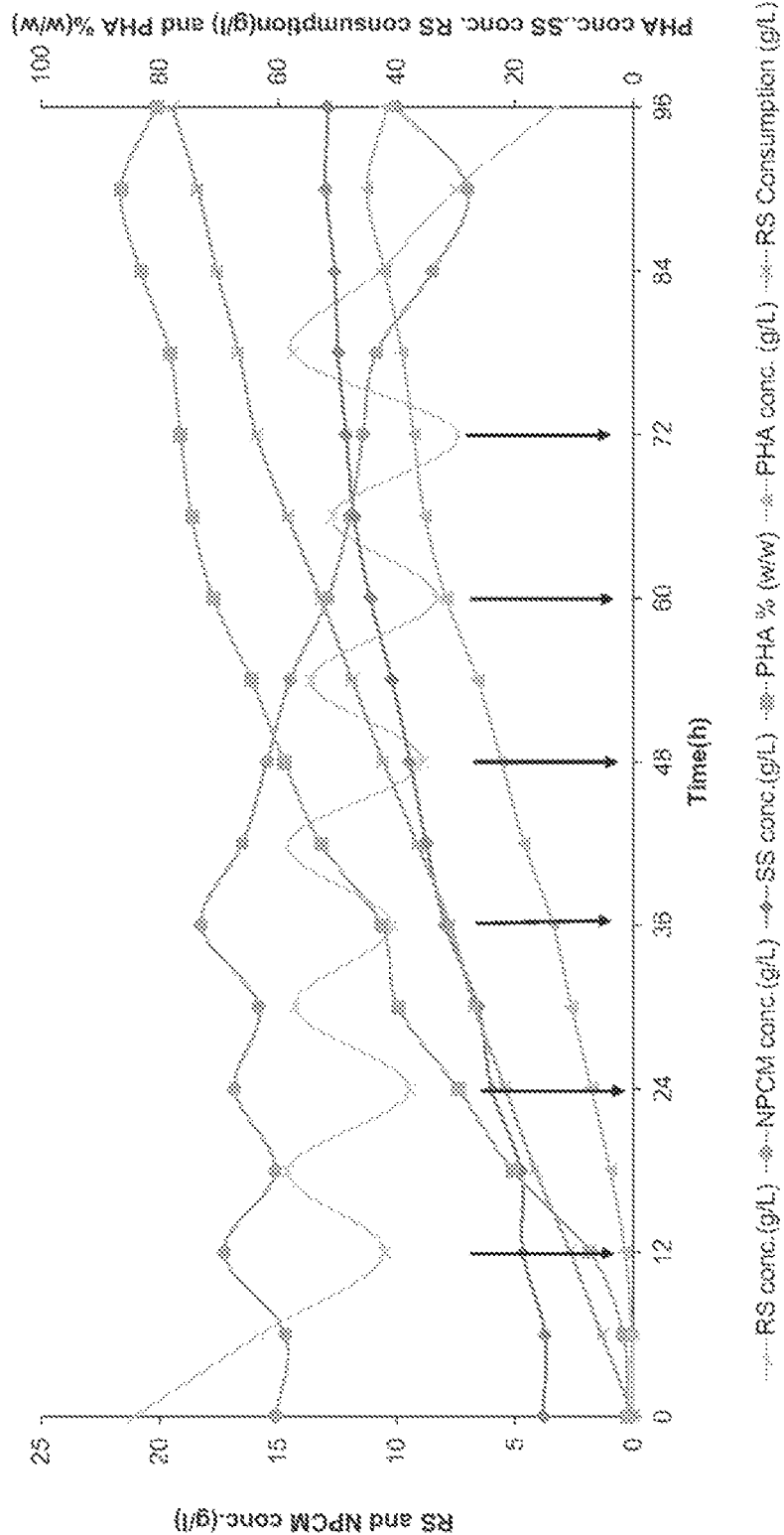
FIGURE 6. Profile of SS, RS concentration, RS consumption, NPCM, PHA concentration and PHA content during fed-batch fermentation for washed and Ca(OH)₂ treated Pulp and paper sludge (15g/L) fortified with glucose (Arrow in the figure represents the points when feed of glucose and salts was added)

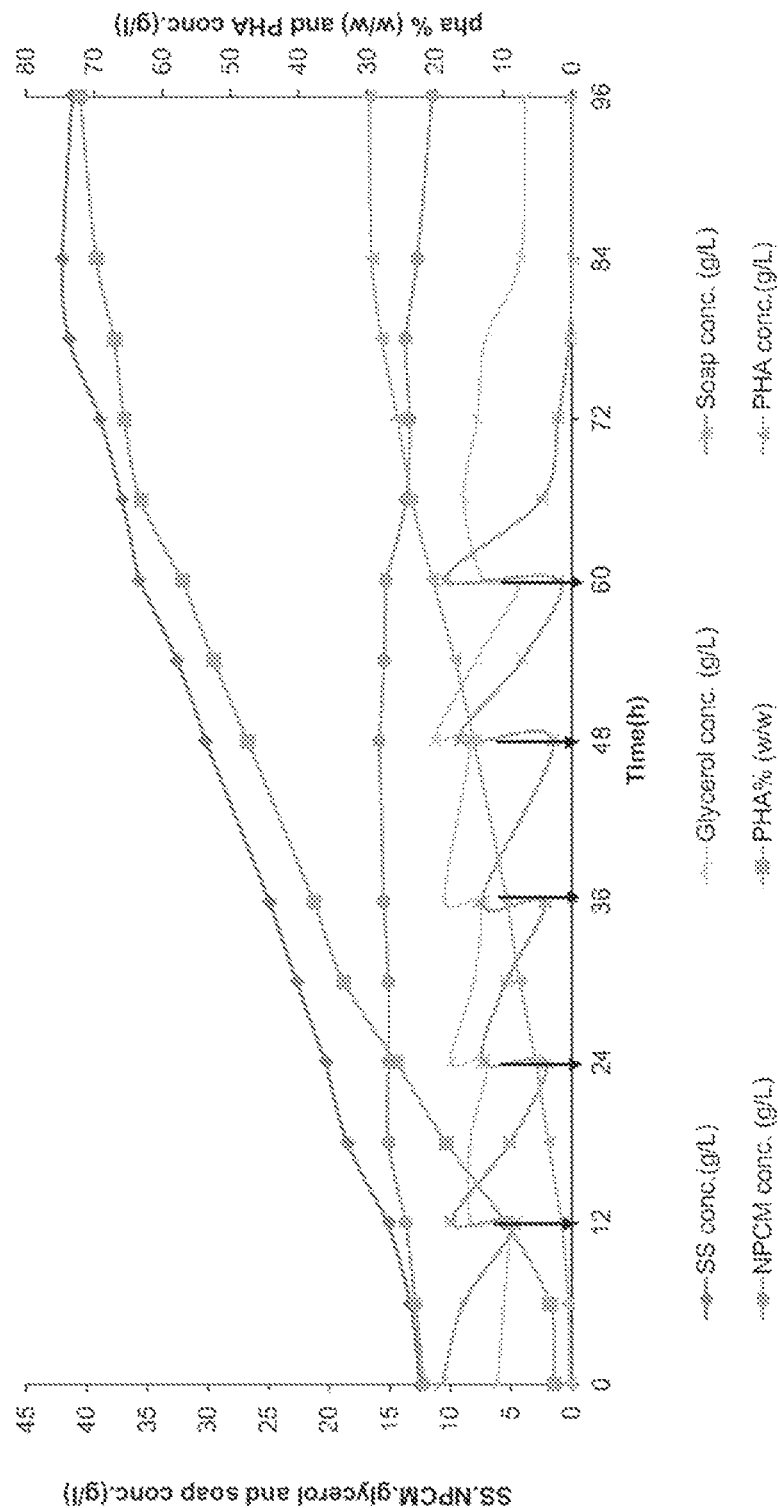
FIGURE 7. Profile of SS, Glycerol and soap concentration, NPCM, PHA concentration and PHA content during fed-batch fermentation for washed and Ca(OH)2 treated Pulp and paper sludge (15g/L) fortified with crude glycerol solution

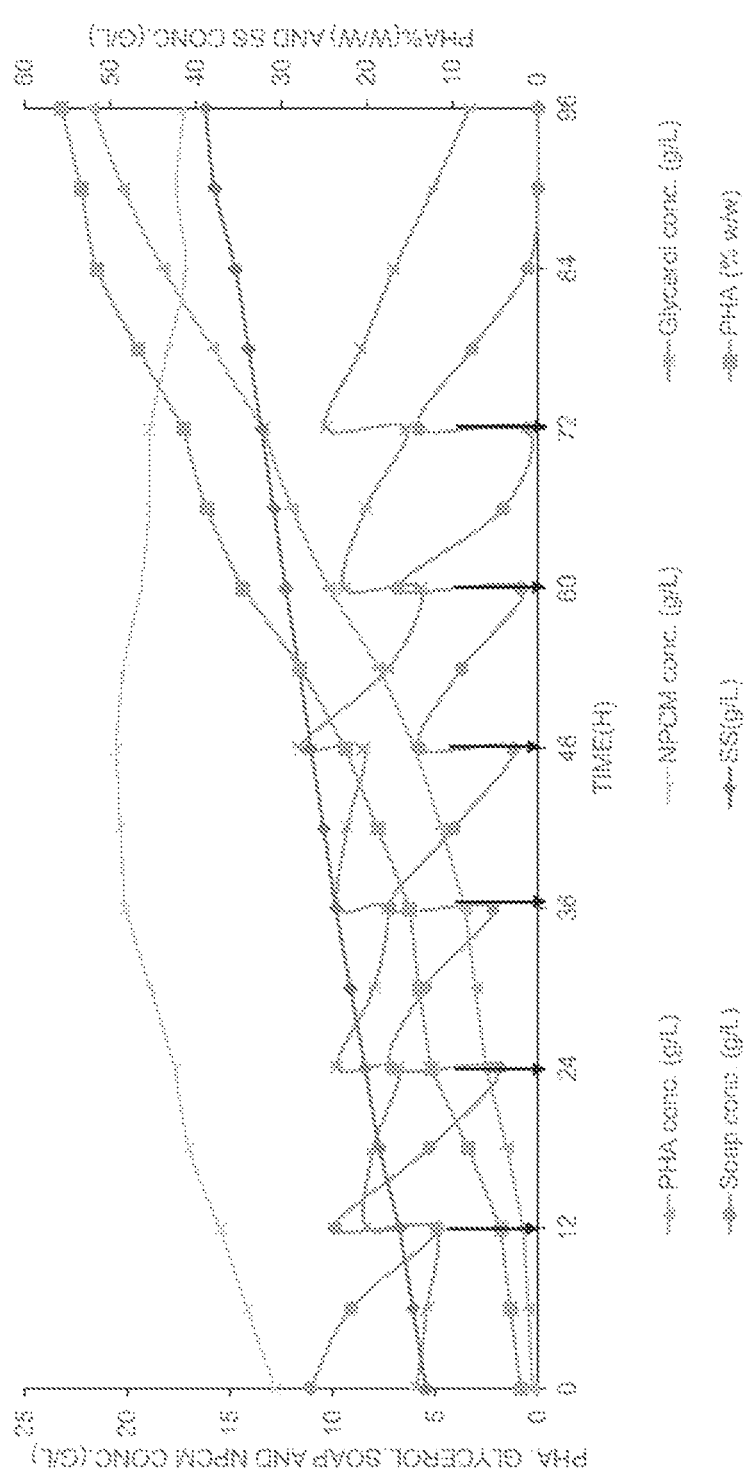
FIGURE 8. Profile of SS, Glycerol and soap concentration, NPCM, PHA concentration and PHA content during fed-batch fermentation process for unwashed and Ca(OH)2 treated Pulp and paper sludge (15g/L) fortified with crude glycerol solution

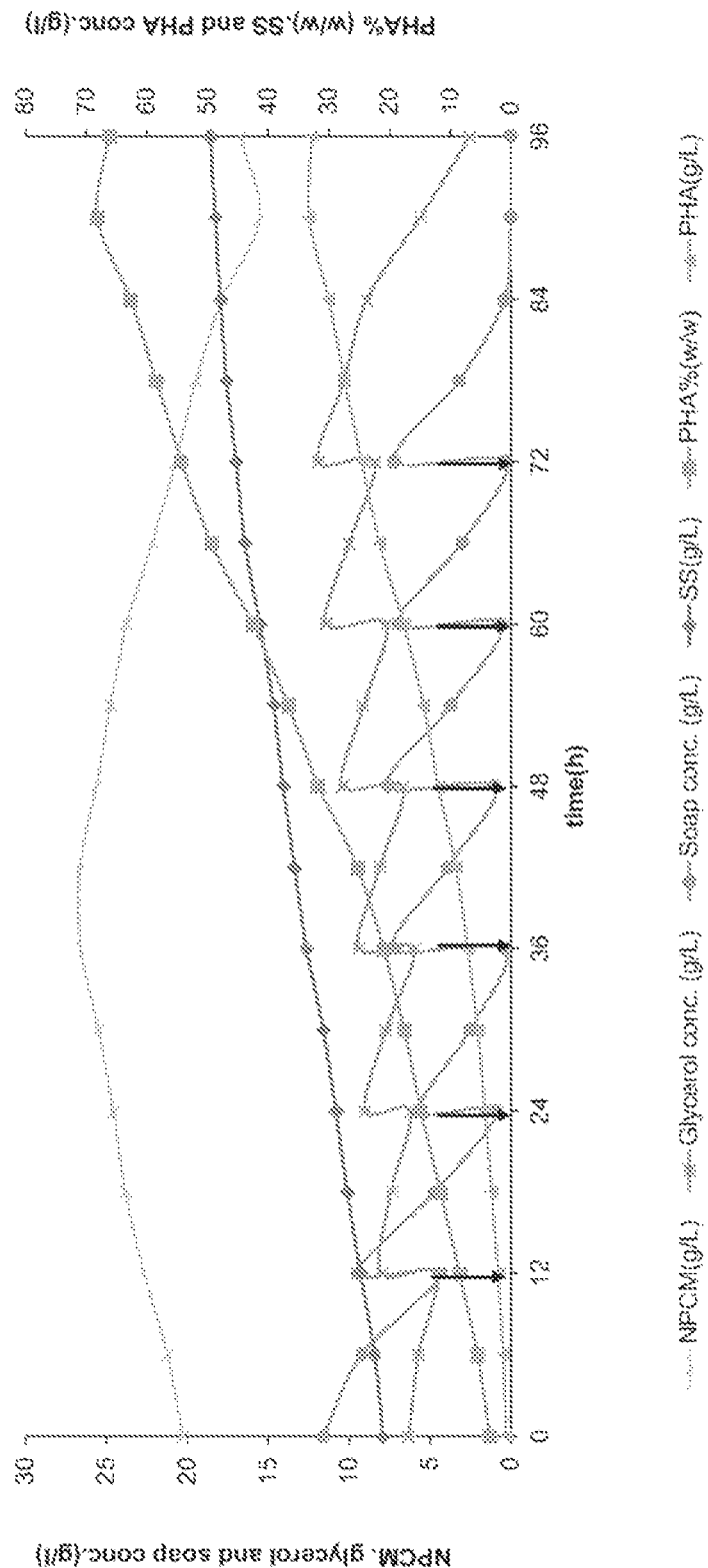
FIGURE 9. Profile of SS, Glycerol and soap concentration, NPCM, PHA concentration and PHA content during fed-batch fermentation process for washed and Ca(OH)2 treated Pulp and paper sludge (25g/L) fortified with crude glycerol solution

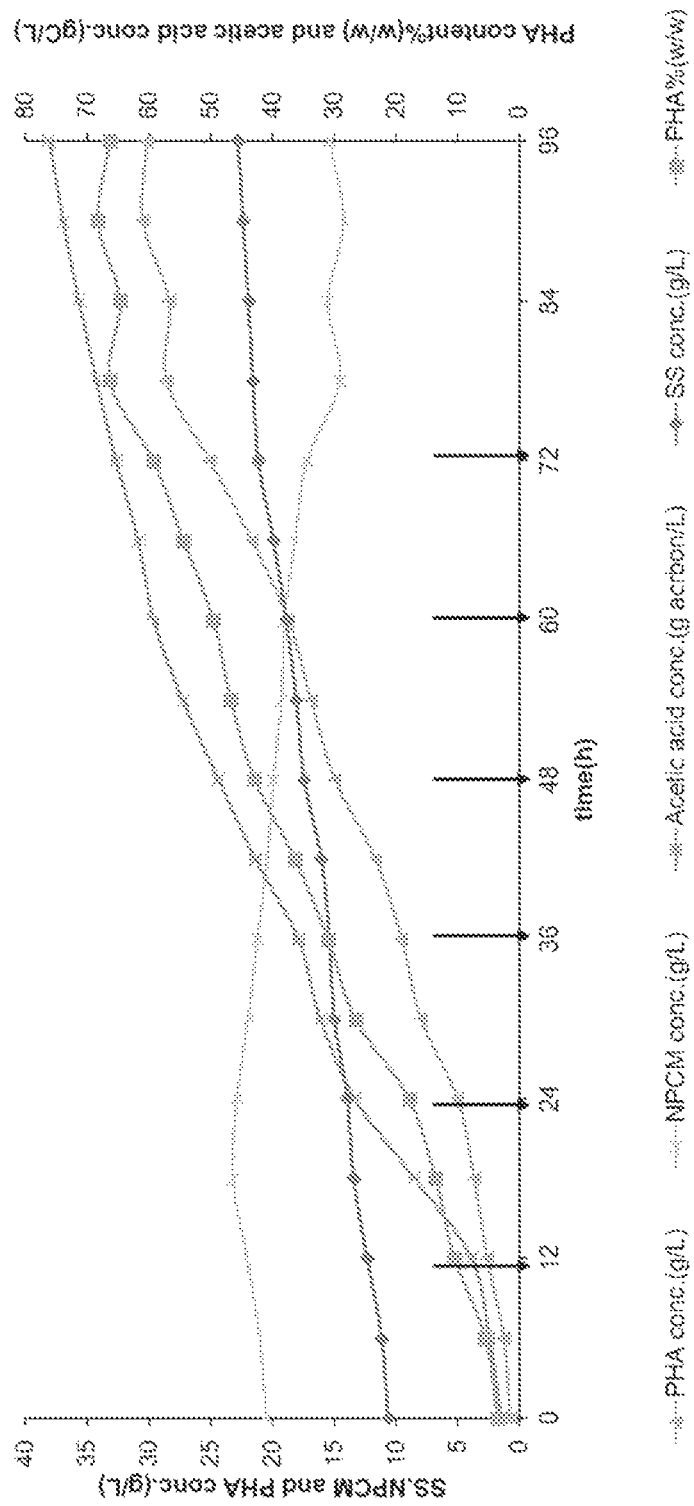
FIGURE 10. Profile of biomass PHA content and SS, PHA, NPCM and acetic acid concentration during fed batch fermentation for Ca(OH)2 treated washed Pulp and paper sludge (25g/L) fortified with acetic acid (6N)

PRODUCTION OF POLYHYDROXYALCANOATES FROM PULP AND PAPER WASTE STREAMS

FIELD

The technical field generally relates to the field of bioplastics. More particularly, the technical field relates to the production of polyhydroxyalkanoates from waste, such as waste streams from pulp and paper production.

BACKGROUND

Polyhydroxyalkanoates (PHA) are a family of biodegradable and biocompatible thermoplastics which can be produced by microorganisms. Typically, cost efficiency in biopolymer production, and particularly in PHA production, is determined by the price for required raw materials. For example, the price of the raw materials can represent up to 50% of the costs. Therefore, in order to reach economic feasibility of PHA production, there is a need for developing efficient fermentation processes by using inexpensive carbon sources from waste materials.

SUMMARY

In one aspect, there is provided a process for producing polyhydroxyalkanoates (PHA), comprising: providing a waste stream comprising lignocellulosic materials; adding a calcium-containing mineral to the waste stream; heat-treating the waste stream in the presence of the calcium-containing mineral, to sterilize the waste stream and obtain a treated waste stream; fermenting at least one strain of PHA-producing microorganism in a culture medium comprising the treated waste stream as a carbon source, to produce the PHA; and extracting the PHA from the PHA-producing microorganism.

In another aspect, there is provided a process for preparing a carbon source for production of polyhydroxyalkanoates (PHA), the process comprising, providing a waste stream comprising lignocellulosic materials; adding a calcium-containing mineral to the waste stream; heat-treating the waste stream in the presence of the calcium-containing mineral, to sterilize the waste stream and obtain a treated waste stream as the carbon source for the production of PHA.

In some implementations, the waste stream is a pulp and paper activated sludge stream.

In some implementations, the calcium-containing mineral comprises at least one of calcium carbonate, calcium hydroxide and calcium oxide.

In some implementations, the calcium-containing mineral comprises calcium hydroxide.

In some implementations, the calcium-containing mineral comprises lime.

In some implementations, adding the calcium-containing mineral to the waste stream is performed prior to the heat-treating of the waste stream.

In some implementations, adding the calcium-containing mineral to the waste stream is performed during the heat-treating of the waste stream.

In some implementations, heat-treating the waste stream is performed at a temperature of at least 120° C.

In some implementations, the process further comprises filtering the waste stream to remove coarse fibers, prior to adding the calcium-containing mineral to the waste stream, thereby obtaining a waste stream filtrate.

In some implementations, the process further comprises settling the waste stream filtrate to decant unfiltered solids, prior to adding the calcium-containing mineral to the waste stream, thereby obtaining a decanted waste stream.

In some implementations, the process further comprises, prior to adding the calcium-containing mineral to the waste stream, washing the decanted waste stream to obtain washed solids.

In some implementations: washing One decanted waste stream comprises: centrifuging the decanted waste stream to obtain centrifuged solids.

In some implementations, the process further comprises: re-suspending the centrifuged solids in an aqueous medium, to obtain a suspension; and re-centrifuging the suspension to obtain the centrifuged solids.

In some implementations, the process further comprises, prior to adding the calcium-containing mineral to the waste stream: adjusting a suspended solids (SS) concentration in the waste stream to a pre-determined concentration, to obtain a conditioned waste stream; and adding the calcium-containing mineral to the conditioned waste stream, wherein heat-treating the waste stream comprises heat-treating the conditioned waste stream.

In some implementations, adjusting the SS concentration is performed on the washed solids.

In some implementations, the pre-determined concentration is between 5 g/L to 50 g/L.

In some implementations, the pre-determined concentration is between 10 g/L to 20 g/L.

In some implementations, the process further comprises adding a secondary carbon source to the culture medium, prior to and/or during the fermentation step.

In some implementations, the secondary carbon source comprises a carboxylic acid, a saccharide, an oil, an alcohol or a combination thereof.

In some implementations, the carboxylic acid comprises acetic acid, propionic acid, butyric acid, valeric add, a salt thereof or a combination thereof.

In some implementations, the saccharide comprises glucose, mannitol, sucrose or a combination thereof.

In some implementations, the oil comprises olive oil, corn oil, palm oil or a combination thereof.

In some implementations, the alcohol comprises glycerol.

In some implementations, the fermentation step comprises maintaining the pH of the waste stream between 6.5 and 7.5 and/or maintaining the temperature between 25° C. and 35° C.

In some implementations, the process further comprises adding a minerals source to the culture medium, prior to and/or during the fermentation step.

In some implementations, the at least one strain of PHA-producing microorganism is a single strain of PHA-producing microorganism.

In some implementations, the at least one strain of PHA-producing microorganism is selected from the group consisting of *Bacillus megaterium, Comamonas testosteroni, Cupriavidus necator* 11599, *Cupriavidus necator* H16, *Pseudomonas guezennei* biovar *Tikehau, R. eutropha, E. coli*, engineered *E. coli, Alcaligenes latus, Sphingobacterium* sp. ATM, *Plasticicumulans acidivorans, Bacillus tequilensis, Hatoferax mediterranei, H. mediterranei, Pseudomonas fluorescens* A2a5 and *Ralstonia eutropha* H16.

In some implementations, extracting the PHA from the PHA-producing microorganisms comprises heat-treating the fermentation mixture so as to lyse at least a portion of the PHA-producing microorganisms, thereby releasing the PHA.

In some implementations, heat-treating the fermentation mixture is performed at a temperature between 80° C. and 125° C.

In some implementations, the process further comprises drying the extraction mixture comprising the PHA.

In some implementations, the process further maintaining a carbon concentration in the culture medium at an optimum carbon concentration based on a carbon consumption of the PHA-producing microorganism.

BRIEF DESCRIPTION OF THE DRAWINGS

FIG. 5 is a graph showing a comparison between growth of PHA-producing microorganisms m a synthetic medium Vs a sludge medium fortified with glucose;

FIG. 6 is a graph showing various parameters observed during PHA production as a function of time during fed-batch fermentation, using a carbon source comprising a conditioned waste stream treated with $Ca(OH)_2$ and glucose;

FIG. 7 is a graph showing various parameters observed during PHA production as a function of time during fed-batch fermentation, using a carbon source comprising a conditioned (washed) waste stream boated with $Ca(OH)_2$ and crude glycerol, FIG. 8 is a graph showing various parameters observed during PHA production as a function of time during fed-batch fermentation, using a carbon source comprising a unconditioned (unwashed) waste stream treated with $Ca(OH)_2$ and crude glycerol;

FIG. 9 is a graph showing various parameters observed during PHA production as a function of time during fed-batch fermentation, using a carbon source comprising a conditioned waste stream with high suspended solids concentration treated with Ca(OH) 2 and crude glycerol; and FIG. 10 is a graph showing various parameters observed during PHA production as a function of time during fed-batch fermentation, using a carbon source comprising a conditioned waste stream with high suspended solids concentration treated with Ca(OH) 2 and acetic acid.

DETAILED DESCRIPTION

As discussed above, there is a need for improved techniques in the production of PHA from waste stream sources (municipal or industrial such as pulp and paper industry activated sludge). These waste stream sources can be taken in to account due to i) their high content in nutrients and complex carbon sources and ii) the possibility of solving sludge disposal problems in the pulp and paper industry, which can account for as much as 60% of total wastewater treatment costs.

The cost of secondary sludge disposal is expected to increase particularly in North America and Europe, in response to higher wastewater treatment standards, reduced landfill capacities and increased in fuel costs.

Researchers are continuously trying to solve the issue of secondary sludge disposal and high PHA production cost by utilizing non-sterile pulp and paper mill activated sludge (PPMAS) directly for PHA production. PHA production processes based on mixed microbial cultures (i.e. activated sludge) has been investigated as a possible technology to solve the issues associated with the cost of maintaining sterile conditions, synthetic medium preparation, and maintenance of pure cultures (Singh et al., 2014) In this process, the main problem is the batch to batch variation of the PHA concentration. Thus, the PHAs production (accumulation) is not reproducible (for the sludge collected at different time from the same wastewater treatment plant as well as sludge collected from different wastewater treatment plant). The variation in PHA accumulation could be attributed to change in composition of microbial community in sludge and chemical composition of activated sludge, which further depends on nature of the process used for pulp and paper production inside the pulp and paper mill. Moreover, the sludge microbial communities are sensitive to changes in the wastewater treatment process parameters like organic feed load, chemical addition, change in SRT, HRT, temperatures, pH of operation, etc.

Various techniques that are described herein enable the synthesis of PHA using waste stream soirees as a nutrient and carbon source. A non-limiting example of a waste stream source is pulp and paper activated sludge.

Overview of the Process

Figure 1:
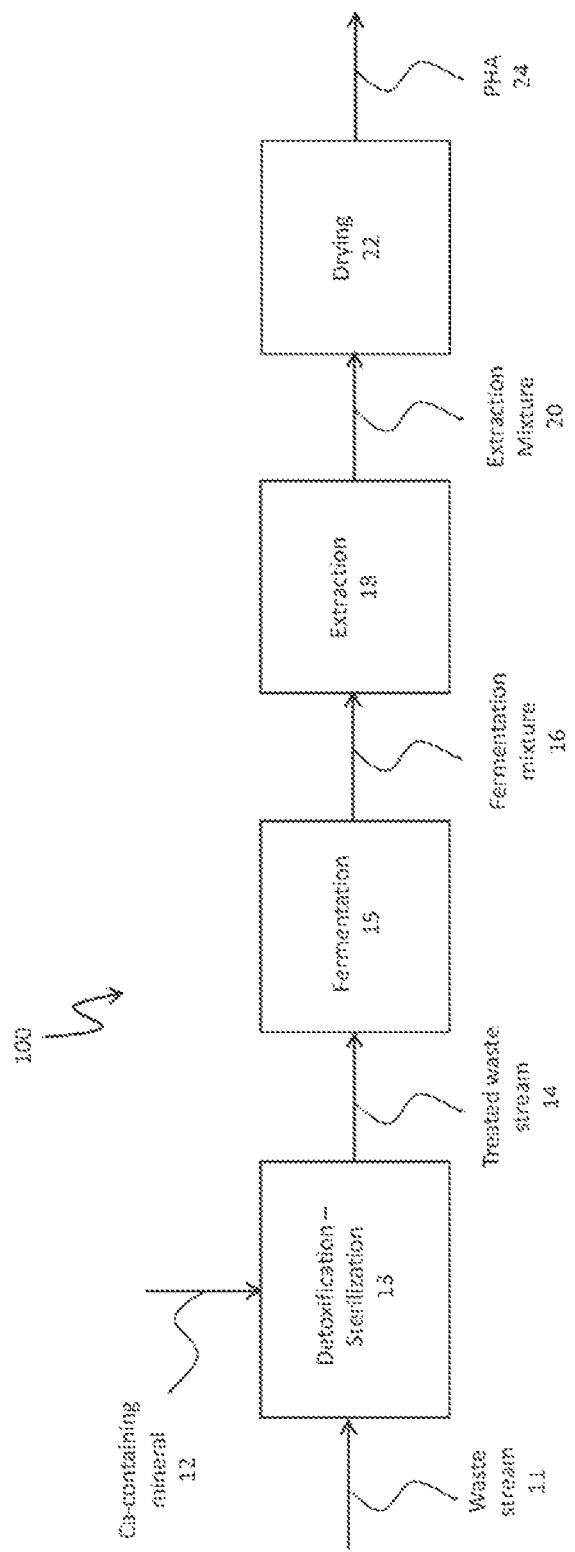
FIG. 1 is a process flow diagram of a process for the synthesis of PHA using a waste stream as a carbon source.

Referring to FIG. 1, a process 100 for the synthesis of PHA using waste stream source 11 is provided. The waste stream 11 can for example include a pulp and paper activated sludge stream, or a stream derived from a pulp and paper activated sludge stream. It should be understood that the expression "stream derived from a pulp and paper activated sludge stream" refers to a sludge stream that is pretreated or conditioned using one or several steps selected from filtration, settling, decantation, centrifugation, washing, suspending in an aqueous medium (e.g., water) and adjusting a suspended solids concentration. For example, the waste stream 11 can be a pulp and paper activated sludge stream originating from a pulp and paper manufacturing plant.

The waste stream 11 includes several carbon-containing compounds that can be used as a carbon source and other nutrients for the production of PHA. A calcium-containing mineral 12 can be added to the waste stream 11 to mitigate the inhibitory effect of certain materials such as hydrolyzed lignocellulosic materials that can be present in the waste stream 11 or be formed during processing of the waste stream 11. The waste stream 11 can be heat-treated in heat-treatment step 13 (also referred to herein as a sterilization step or a detoxification step) in the presence of the calcium-containing mineral 12, to sterilize the waste stream and obtain a treated waste stream 14.

It has been surprisingly found that adding the calcium-containing mineral 12 to the waste stream 11 prior to or during the heat-treatment step 13 can help solubilizing sludge suspended solids and making nutrients more readily available to PHA-producing microorganisms. Furthermore, it has been surprisingly found that adding the calcium-containing mineral 12 to the waste stream 11 prior to or during the heat-treatment step 13 can help decrease the inhibitory materials typically generated during the heat-treatment as a result of the hydrolysis of the lignocellulosic materials initially present in the waste stream.

The treated waste stream 14 can then be fermented in a fermentation step 15 to obtain a fermentation mixture 16 and extracted in an extraction step 18 to obtain an extraction mixture 20 comprising the PHA 24. Optionally, a drying step 22 can be performed to dry the PHA 24.

Figure 2:
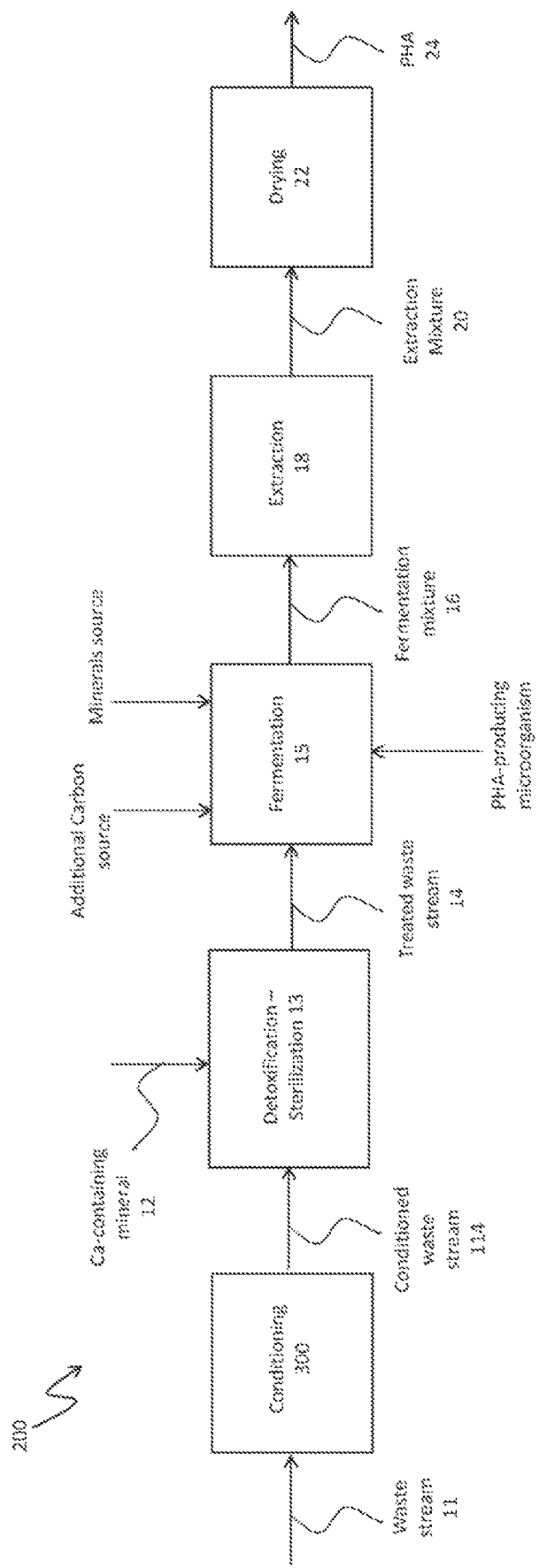
FIG. 2 is a process flow diagram of the process of FIG. 1, wherein the waste stream is conditioned prior to adding the calcium-containing mineral.

The waste stream 11 can be subjected to the heat-treatment step 13 directly, as shown in process 100 of FIG. 1. Alternatively, the waste stream 11 can be conditioned in a conditioning process 300 prior to the heat-treatment step 13, as shown in process 200 of FIG. 2. In such case, it is the conditioned waste stream 114 that is subjected to the heat-treatment step 13. The conditioning process 300 will be discussed in further detail herein.

The steps of the process and other aspects of PHA production techniques are described in further detail below.

Polyhydroxyalkanoates (PHA)

It should be understood that the terms "polyhydroxyalkanoates" or "PHA" refer to polymers that can be represented by the following repeating unit of Formula I, or to copolymers comprising monomers of at least two different repeating units of Formula I, wherein R is H, alkyl or alkenyl, and m and n are integers.

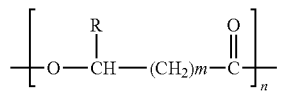

Formula I

Some PHAs have found industrial application, with non-limiting representatives being the PHB (poly-3-hydroxybutyrate), PHBV (poly(hydroxybutyrate-co-hydroxyvalerate)), P4HB (poly(4-hydroxybutyrate), P3HB4HB (poly(3-hydroxybutyrate-co-4-hydroxybutyrate)), PHV (polyhydroxyvalerate), and PHHx (polyhydroxyhexanoate).

Optionally, n can be an integer between 100 and 30000. Optionally, m can be an integer between 1 and 4 Optionally, R can be H, alkyl, substituted alkyl, alkenyl or substituted alkenyl. For example, R can be H, methyl, ethyl, propyl or butyl.

Waste Stream Sources

It should be understood that the waste stream 11 can originate from various sources. In some implementations, the waste stream 11 is obtained from municipal waste water, starch manufacturing waste water, cheese manufacturing waste water, a waste stream from pulp and paper production or a combination thereof. Additionally, any one of the waste streams referred to herein can be obtained from primary sludge, secondary sludge or a combination thereof. It is understood that "primary sludge" is a result of the capture of suspended solids and organics in a primary treatment process mainly through gravitational separation, which can for example be done in a primary clarifier. It is also understood that "secondary sludge" is obtained by treating waste water in a secondary treatment process which uses microorganisms to consume organic matter present in the waste water. The microorganisms typically feed on biodegradable material present in the waste water, for example in an aeration tank, and then flow into a secondary clarifier where biomass can settle out and be removed as secondary sludge. As a result of the process from which the waste stream originates, as well as microorganism activity, the waste stream 11 typically contains organic material that can be used as carbon source few PHA-producing microorganisms for producing PHA In some implementations, the waste stream is a waste stream from pulp and paper production. Optionally, the waste stream from pulp and paper production includes a secondary waste stream. Optionally, the waste stream from pulp and paper production consists essentially of a secondary waste stream. Secondary or activated sludge discharged from the wastewater treatment plant can be used as a waste material for PHA production. In some scenarios, activated sludge can be combined with other carbon sources (such as crude glycerol—a waste product of biodiesel industry, glucose, acetic add, waste cooking oil, or similar municipal or industrial wastes, etc).

Conditioning of the Waste Stream

Figure 3:
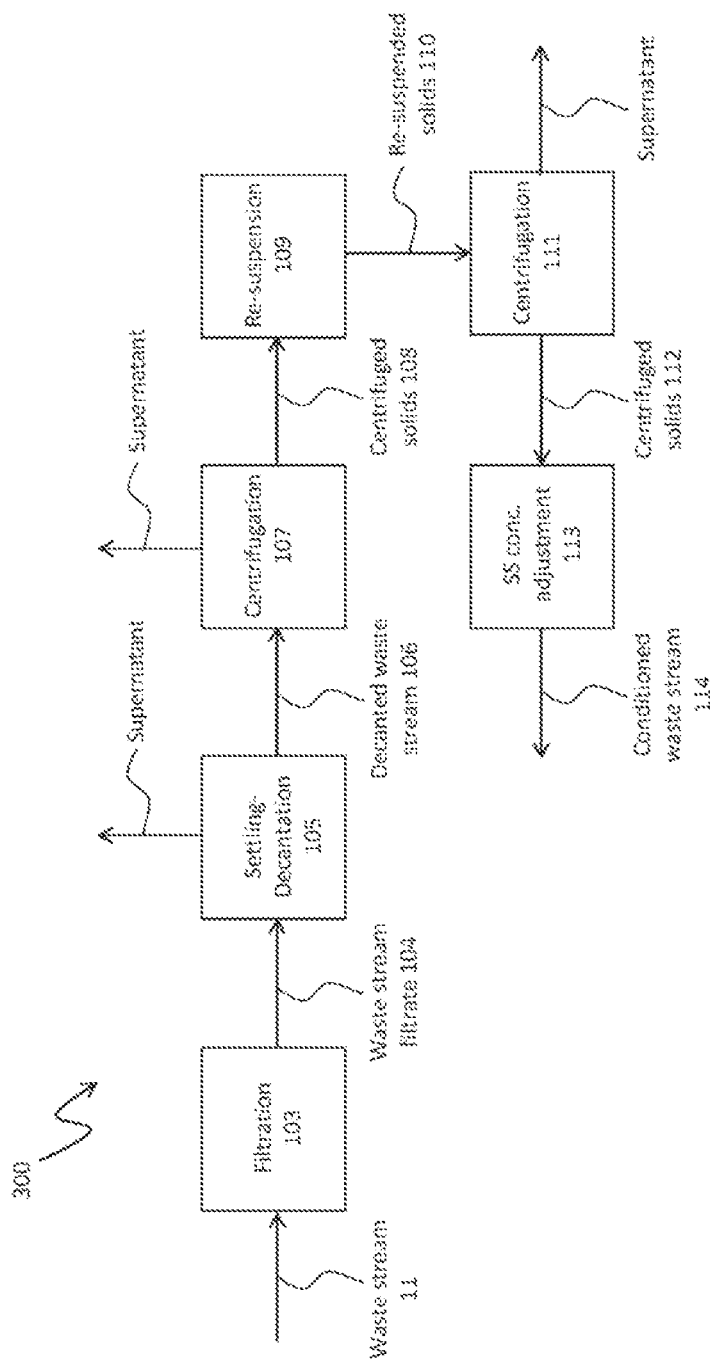
FIG. 3 is a process flow diagram showing various steps of the conditioning process.
Figure 4:
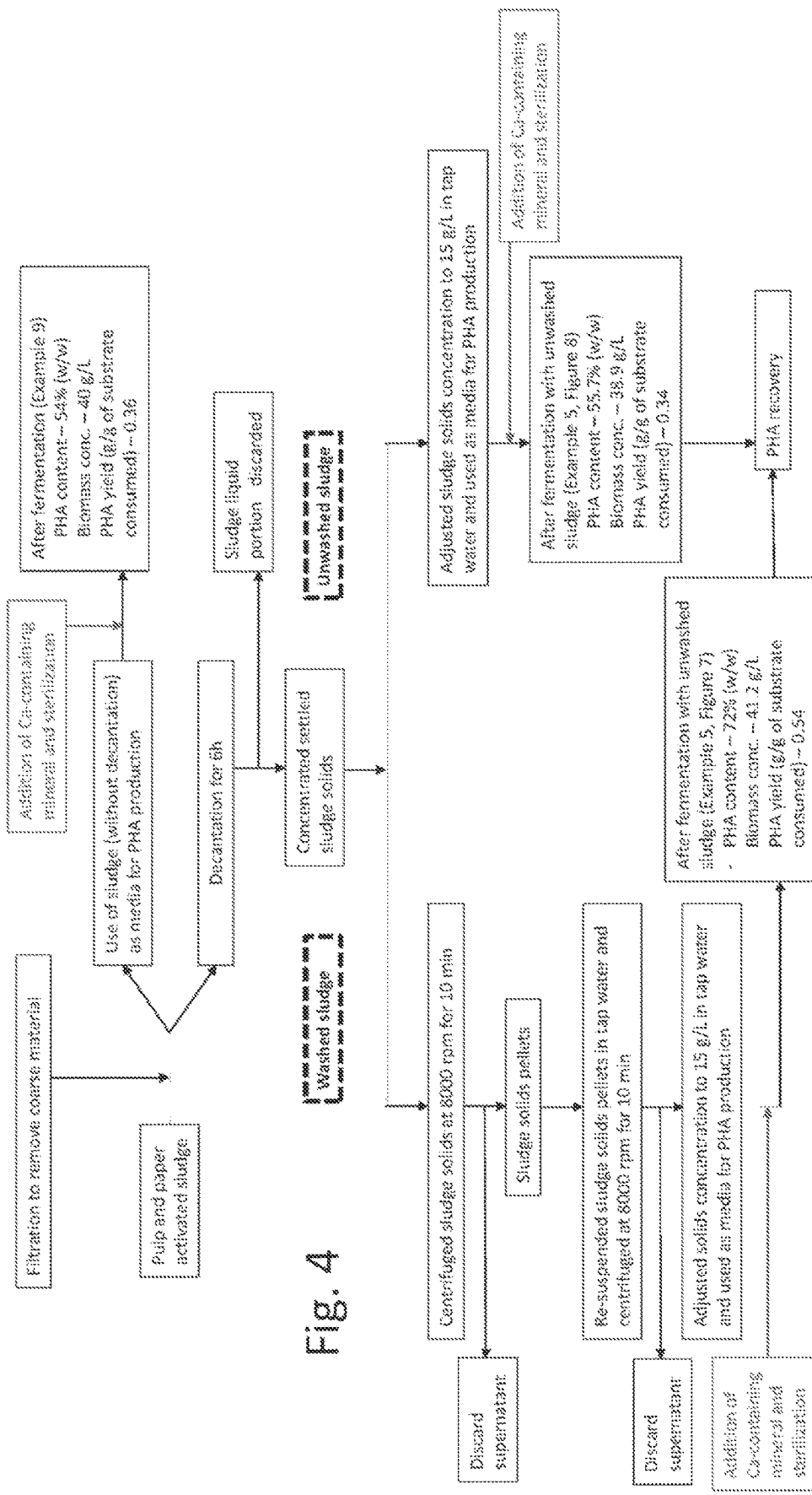
FIG. 4 is a flow chart showing various steps and conditions to synthesize PHA using a waste stream as a carbon source.

Now referring to FIG. 3, a process 300 few conditioning the waste stream 11 for subsequent PHA production is shown. The waste stream 11 can be conditioned prior to adding the calcium-containing mineral, and prior to the heat-treatment step 13 and the fermentation step 15.

In some implementations, the waste stream 11 is subjected to a filtration step 103 prior to adding the calcium-containing mineral 12, to obtain a waste stream filtrate 104. The filtration step 103 can enable the removal of coarse material such as wood residues and/or coarse fibers that can initially be present in the waste stream 11. For example, the filtration step 103 can be performed using a 100 mm to 1500 mm filter, or a 500 mm to 1000 mm filter, or a 700 mm to 900 mm filter, or an 800 mm filter.

In some implementations, the waste stream filtrate 104 can be subjected to a settling step or decantation step 105 prior to adding the calcium-containing mineral 12 to the waste stream, to obtain a decanted waste stream 106. The settling step or decantation step 105 can include decanting the waste stream filtrate 104 for several hours, such as between 2 hours and 12 hours, or between 5 hours and 7 hours, or for about 6 hours. The decantation of the waste stream filtrate 104 allows for decanting unfiltered solids. In some implementations, the sludge liquid portion can be discarded, and the decanted waste stream 106 can mainly mostly include concentrated settled sludge solids. In some scenarios, the concentrated settled sludge solids are obtained by discarding the sludge liquid portion without further drying or processing of the remaining solids.

In some implementations, the decanted waste stream 106 can be washed. Washing the decanted waste stream 106 can include a centrifugation step 107 prior to adding the calcium-containing mineral 12 to the waste stream, to obtain centrifuged solids 108. In some implementations, washing the decanted waste stream 106 further includes re-suspending the centrifuged solids in an aqueous medium (e.g., water) in a suspension step 109, to obtain re-suspended solids 110. In some implementations, washing the decanted waste stream 106 further includes re-centrifuging the re-suspended solids 110 in a second centrifugation step 111 to obtain centrifuged solids 112.

In some implementations, the liquid portion (or supernatant) obtained after the decantation step 105, first centrifugation step 107 and/or second centrifugation step 111 can be discarded. The solids fraction obtained after the decantation step 105, first centrifugation step 107 and/or second centrifugation step 111 can optionally be resuspended in an aqueous medium (e.g., water) prior to a subsequent step.

It should also be understood that each one of the conditioning steps described herein is optional and do not necessarily need to be performed in order to obtain the treated waste stream 14 after the detoxification step 13. For example, in some scenarios, the settling or decantation step 105 can be omitted, and the first centrifugation step 107 can be performed directly on the waste stream filtrate 104. In some scenarios, the waste stream 11 may not require a filtration step 103 (for example, in instances where there are no or few coarse materials to be filtered). In another example, the suspension step 109 can be performed directly on the decanted waste stream 106 and the centrifugation step 107 can be omitted. It should also be understood that m some scenarios, the second centrifugation step 111 can also be omitted. In some scenarios, only a single centrifugation step can be performed. In other scenarios, two or more centrifugation steps can be performed.

In some implementations, the first and/or second centrifugation steps are performed at between 8000×g and 10000×g. In some implementations, the first and/or second centrifugation steps are performed at room temperature (20-25° C.). In some implementations, the first and/or second centrifugation steps are performed for between 5 mins and 20 mins.

In some implementations; the conditioning of the waste stream 11 further comprises adjusting a suspended solids (SS) concentration a pre-determined concentration. In some implementations, file pre-determined concentration is between 5 g/L to 50 g/L, or between 10 g/L to 20 g/L, or again at about 15 g/L. In some implementations, the suspended solids concentration is adjusted by addition of an aqueous medium (e.g.; water). Adjusting the SS concentration can be performed directly on the waste stream 11 or after the last step performed in the conditioning process. In other words, adjusting the SS concentration can be performed on one of the waste stream 11, waste stream filtrate 104, decanted waste stream 106, centrifuged solids 108, re-suspended solids 110 or centrifuged solids 112, depending on which stream is the last stream obtained in the conditioning process 300.

Calcium-Containing Mineral and Heat-Treatment Step

When the waste stream 11 is a pulp and paper activated sludge stream, or a stream derived from the treatment of various natural materials originating from various wood sources or plants (e.g., wood, wheat, rice etc.), the organic materials include lignocellulosic materials. When the lignocellulosic materials are hydrolyzed, several hydrolysis products are released and can be inhibitory to PHA production. It has been surprisingly found that adding the calcium-containing mineral 12 to the waste stream 11 or to the conditioned waste stream 114 prior to or during the heat-treatment step 13 can help solubilizing sludge suspended solids and increase nutrient availability to file PHA-producing microorganisms. Furthermore, it has been surprisingly found that adding the calcium-containing mineral 12 to the waste stream 11 or to the conditioned waste stream 114 prior to or during the heat-treatment step 13 can help decrease the inhibitory materials typically generated during file heat-treatment as a result of the hydrolysis of the lignocellulosic materials initially present in the waste stream 11.

Non-limiting examples of calcium-containing mineral 12 include calcium carbonate, calcium hydroxide, calcium oxide, lime or a mixture thereof. Preferably, the calcium-containing mineral includes calcium hydroxide.

It should be understood that the heat-treatment step 13 is typically a sterilization step (i.e., heating at high enough temperatures and for a long enough time to kill or inactivate microorganisms (e.g., bacteria) present in the waste stream 11 or the conditioned waste stream 114). In some implementations, the heat-treatment of the waste stream 11 or the conditioned waste stream 114 is performed at a temperature of at least 120° C.

In some implementations, the amount of Ca-containing mineral that is added based on the SS concentration. For example, between 0.05 g and 0.5 g, or between 0.05 g and 0.2 g. or between 01 g and 0.2 g, or about 0.1 g of Ca-containing mineral can be added for each g of SS solids present in the waste stream 11 or the conditioned waste stream 114, depending on when the Ca-containing mineral is added. More particularly, between about 0.05 g and 0.5 g, or between 0.05 g and 0.2 g, or between 0.1 g and 0.2 g, or about 0.1 g of calcium hydroxide, calcium carbonate, calcium oxide or lime can be added to the waste stream 11 or the conditioned waste stream 114. It should be understood that the SS solids concentration can be measured using standardized protocols such as ASTM-D 5907, EPA 180.1 and/or ISO 7027.

Fermentation Step

After the waste stream 11 or the conditioned waste stream 114 is sterilized in the presence of the Ca-containing mineral, the treated waste stream 14 is fermented in a fermentation step 15.

In some implementations, the fermentation step 15 can include a batch fermentation, a fed-batch fermentation, an open fermentation and/or a continuous fermentation. Preferably, the fermentation step 15 includes a fed-batch fermentation. In some scenarios, the fermentation step 15 consists of a fed-batch fermentation. It should be understood that the term "fed-batch fermentation", as used herein, refers to a variation of the batch fermentation, where some of the ingredients are added during the fermentation. This typically allows for a greater control over the stages of the fermentation process. In particular, production of secondary metabolites may be increased by adding a limited quantity of certain nutrients during the non-exponential growth phase. In some implementations, the fermentation step 15 includes fed-batch operations sandwiched between batch operations.

In some implementations, the fermentation step 15 is carried out at a temperature between 20° C. and 40° C. It should also be understood that the temperature can be selected based on the bacterial strain or strains used as PHA-producing microorganisms. In some implementations, the heat-treatment of the waste stream 11 or conditioned waste stream 114 can be performed in the presence of toe Ca-containing mineral. In such case, the fermenter can be heated at toe desired temperature for heat-treatment, and then cooled down to the fermentation temperature.

In some implementations, the fermentation step comprises maintaining the pH of the waste stream between 6.5 and 7.5 and/or maintaining the temperature between 25° C. and 35° C.

In some implementations, a secondary carbon source can be added to the culture medium, prior to and/or during toe fermentation step 15. Similarly, a minerals source can be added to the culture medium, prior to and/or during the fermentation step 15. The PHA-producing microorganisms are also typically added to the culture medium prior to and/or during the fermentation step 15.

PHA-Producing Microorganisms

The PHA-producing microorganism can be any bacterial strain that is known to produce PHA. Non-limiting examples of PHA producing microorganisms are listed in Table 1 below.

TABLE 1

List of PHA producing microorganisms

| Strain | PHA content (% w/w) |
|---|---|
| *Bacillus megaterium* | 50 |
| *Comamonas testosteroni* | 79 |

TABLE 1-continued

List of PHA producing microorganisms

| Strain | PHA content (% w/w) |
|---|---|
| Cupriavidus necator 11599 | 90 |
| Cupriavidus necator H16 | 80 |
| Pseudomonas guezennei biovar tikehau | 63 |
| R. eutropha | 76 |
| E. coli (engineered) | 75 |
| Alcaligenes latus | 77.6 |
| Sphingobacterium sp. ATM | 64 |
| Plasticicumulans acidivorans | 70 |
| Bacillus tequilensis | 79.2 |
| Haloferax mediterranei | 65 |
| H. mediterranei | 75 |
| Pseudomonas fluorescens A2a5 | 70 |
| Ralstonia eutropha H16 | 76 |

In some implementations, the cell count in the pre-inoculum for bacterial strains can be between $10^8$ to $10^9$ grown for 24 h. However, it should be understood that a lower or higher cell count in the pre-inoculum is possible and generally does not affect the process of PHA production to a greater extent.

In some implementations, the PHA-producing microorganisms are cultivated prior to being introduced to the culture medium. For example, PHA-producing microorganisms can be cultivated for 12 hours to 48 hours, or for between 12 hours and 24 hours, or few about 24 hours, prior to being introduced to the culture medium. The pre-inoculum thereby obtained can then be added to the culture medium prior to and/or during the fermentation step 15.

In some implementations, the PHA-producing microorganism is a single strain of PHA-producing microorganism. In other implementations, the PHA-producing microorganism can include more than one strain of PHA-producing microorganism.

Minerals Source

In some implementations, a minerals source can be added to the medium to help PHA production during the fermentation process. Non-limiting examples of minerals that can be added are $NH_4Cl$ (e.g., 0.2-1.0 g/L), $Na_2HPO_4$ (e.g., 0.5-6.0 g/L), $KH_2PO_4$ (e.g., 0.2-2.4 g/L), $MgSO_4 \cdot 7H_2O$ (e.g., 0.04-0.5 g/L), and combinations thereof. The components in the following can be added to the medium to foster PHA production during fermentation process. It should be understood that other minerals can be used and that the concentrations indicated above are given as an example and should not be construed as limiting.

Additional Carbon Source

In some implementations, the process further includes adding a secondary carbon source to the culture medium, prior to and/or during the fermentation step 15. For example, the secondary carbon source can include a carboxylic acid, a saccharide, an oil, an alcohol or a combination thereof. The carboxylic acid can include acetic acid, propionic acid, butyric acid, valeric acid, a salt thereof or a combination thereof. The saccharide can include glucose, mannitol, sucrose or a combination thereof. The oil can include a vegetal oil such as olive oil, corn oil, palm oil or a combination thereof. The alcohol can include glycerol, such as pure or crude glycerol.

Extraction Step

The fermentation mixture 16 that is obtained after the fermentation step 15 contains microbial cells that include PHA 24 which has to be extracted in an extraction step 18. The fermentation step 16 is therefore stopped and the fermentation mixture 16 is further processed in order to recover the PHA 24. In some implementations, the extraction step 18 can include at least one of a heat treatment step, a sonication step and an oxidative treatment step.

The extraction step 18 can include heat treating the fermentation mixture 16 in order to lyse at least a portion of the microbial cells that include PHA. In some scenarios, the PHA contained in the fermentation mixture 16 is degraded by the microbial cells. In such case, the heat treatment applied can help minimize degradation.

In some implementations, when the PHA concentration reaches a maximum (which is for example determined when the rate of consumption of the source of carbon such as acetic acid/acetate becomes constant and has reached a minimum value), the fermentation mixture 16 can be heated (for example to between 80° C. and 125° C., and for example between about 10 minutes to 45 minutes, or between about 15 minutes to 30 minutes). Optionally, during the heating step, a positive concentration of acetic acid can be maintained in the fermenter. This heating step typically lyses at least a portion of the microbial cells, therefore releasing the PHA contained therein. It is understood that the PHA is typically not degraded at these temperatures. It is understood that the expression "the PHA is released from the cells" means that PHA which is initially intracellular PHA, is driven out of the cells due to lysis of the cells/cell disruption caused by the heat treatment (i.e., extracellular PHA is obtained). Furthermore, the PHA concentration can be increased due to solubilization of cellular content, such as solubilization of components of the cell walls.

In some implementations, the heat treating of the fermentation mixture 16 includes a heat treatment enhancement compound it is understood that the heat treatment enhancement compound can allow for the heat treatment to be performed at lower temperatures. In some implementation, the heat treatment enhancement compound includes detergent. In some implementations, the detergent includes a surfactant, a chelating agent or a combination thereof. In some implementations, the detergent includes Tween™ 20, Tween™ 40, Tween™ 60, Sodium 2-dodecyl sulfate, Triton X-100, Ethylene diamine tetra-acetate (EDTA) or a combination thereof. When a detergent is added during the heat treatment of the fermentation mixture 16, the heat treatment can be performed at temperatures between 80° C. and 95° C.

The extraction step 18 to separate PHAs from biomass can be performed using chlorinated solvents such as chloroform, methylene chlorides and/or 1,2-dichloroethane. A combination of these chlorinated solvents with other solvents can also be used for extraction. The extracted PHA can then be separated from the solvent by evaporation of the solvent or by precipitation of the polymer by adding a polar solvent such as acetone or an alcohol (for example methanol or ethanol) Alternatively, non-PHA cellular material can be digested using different chemicals such as alkaline compounds, and the detergents cited above. A detergent-based method for recovering PHA differs from solvent-based extraction in that the detergent can disrupt cell components while leaving the PHA substantially intact.

Another method of initiating cell disruption is the use of sonication, for example by using devices operating between 20 and 40 kHz frequencies, which are commercially available. In some implementations, the fermentation mixture 16 can be sonicated prior to the heat-treatment, during the heat treatment or after the heat treatment. In some implementations, the heat-treated fermentation mixture is sonicated to further break the cells and release PHA into the medium. The sonication can be performed for several minutes, for example between 1 minute and 30 minutes. In some implementations, the sonication is performed for 2 to 5 minutes, or for 3 minutes.

In some implementations, the extraction step 18 can include adding an oxidizing agent to foe fermentation mixture. For example, the oxidizing agent can include a peroxide, a hypochlorite or a combination thereof. In some implementations, foe hypochlorite includes sodium hypochlorite, which can be used at concentrations between 1 and 5% w/v. In some implementations, foe peroxide includes hydrogen peroxides, which can be used at concentrations between 1 and 5% v/v. In some implementations, sodium hypochlorite is used prior to the hydrogen peroxide. It is understood that the use of an oxidizing agent can facilitate decolorization of the fermentation mixture, which in turn can lead to a decolorized PHA. In some implementations, the oxidative treatment is performed after the heat treatment step. In some implementations, the oxidizing step is performed after the sonication step.

In some implementations, extraction step 18 can include centrifugation. For example, centrifugation can be performed after the heat treatment, after the sonication step and/or after one of the oxidative treatments. In some implementations, the extraction process includes several centrifugation steps. For example, a centrifugation step can be performed between the heat treatment step and the sonication step, between the sonication step and the sodium hypochlorite treatment step, and/or between the sodium hypochlorite treatment step and/or the hydrogen peroxide treatment step.

Drying Step

The extraction mixture comprising the PHA can be dried, for example by spray drying.

EXAMPLES

Example 1

Experiments were conducted to compare PHA producing microorganism growth using a synthetic medium (glucose) on the one hand, and a sterilized pulp and paper mill activated sludge (PPMAS) that was fortified with glucose on the other hand.

The experiments started with preparation of first and second pre-inoculum. The first pre-inoculum was prepared by inoculating PHA producing microorganisms from the mineral media agar plates into the mineral media (MM) or synthetic medium (SM) broth containing (per liter of distilled water) 20 g of glucose, 6.0 g of sodium hydrogen phosphate dodecahydrate ($Na_2HPO_4.12H_2O$), 2.4 g of dihydrogen potassium phosphate ($KH_2PO_4$), 1.0 g of ammonium chloride ($NH_4Cl$). 0.50 g of magnesium sulphate heptahydrate ($MgSO_4.7H_2O$) The phosphates ($Na_2HPO_4.12H_2O$, $KH_2PO_4$) and ammonium chloride were sterilized together with glucose, while $MgSO_4.7H_2O$ was autoclaved separately at 121° C. few 15 min and these solutions were mixed aseptically after cooling. Medium pH was maintained at 6.8 and pre-inoculum was maintained at agitation of 150 rpm for 24 h at 30° C. The same composition and cultivation conditions are followed for pre-inoculum 1 in all the given examples.

After this time, 2-10% (v/v) of the pre-inoculum was transferred into each of a) synthetic medium (glucose, 10 g/L) and b) sludge (10 g/L SS (suspended solids) media fortified with 10 g/L of glucose (second pre-inoculum). Other mineral composition was same as first pre-inoculum media. The second pre-inoculum was also maintained at 30° C. 150 rpm for 24 h and thereafter. 2-10% (v/v) of second pre-inoculum was transferred into 200 mL of production medium in 1 L Erlenmeyer shake flasks. The composition of production media was the same as second pre-inoculum media except 15 g/L of SS was used in sludge production media and glucose concentration used in case of both sludge and synthetic production media was 20 g/L. Incubation of production media for PHA production was conducted for 96 h at 30° C. and 150 rpm. The samples from the bacterial fermentation was taken after every 24 h to measure the CFU (colony forming unit).

The microbial growth was one log cycle higher using sterilized PPMAS (pulp and paper milt activated sludge) as a substrate as compared to the synthetic media without addition of sludge (The results are summarized in FIG. 5).

Example 2

Different experiments were conducted in shake flasks for variation of different parameters, and a comparison of microbial growth and PHA production for washed and unwashed sludge was performed. Further variation of sodium hydroxide (NaOH) dosage was dote for maximum solubilization of sludge solids. The selected NaOH dosage was further applied to look into the effect of SS concentration on growth and PHA production.

PHA production using washed (conditioned) and unwashed sludge (without fortification of extra carbon source and minerals): The unidentified components of the sludge matrix can pose reasonable inhibition to the biomass growth and accumulation of PHA. With an assumption that during PHA accumulation, very limited amount of nutrients are required and the nutrients are embedded in the activated sludge solids, Hie sludge was centrifuged and the supernatant thus obtained was discarded and the sludge biomass (or the centrifuged pellet) was re-suspended in tap water to be used as substrate (partial carbon and nutrient source) for PHA accumulation (conditioned sludge). Therefore, sludge production media was prepared using different suspended solids concentration erf unwashed (10, 15, 20, 25, 30 g/L) and washed sludge (15, 20, 25, 30 and 35 g/L) to study their effect on microbial growth and PHA accumulation. The sludge suspended solids were sterilized at 121° C. for 30 min. After sterilization, suspended solids were allowed to cool to room temperature, thereafter, under sterile conditions, pH was adjusted to 6.8 using 4 N NaOH (Sodium hydroxide) or $H_2SO_4$ (Sulfuric acid). All shake flasks were inoculated with 2-10% (v/v) inoculum of pre-culture-2, which was prepared in the same way as production media (various SS concentration of washed and unwashed sludge, without fortification of extra carbon source and minerals) and kept for incubation at 30° C., 150 rpm for 96 h.

The maximum ceil growth and PHA content was obtained using washed sludge with 15 g/L SS (Table 2). Other SS values also allow obtaining a comparable PHA content.

TABLE 2

Comparison between washed and unwashed sludge used for growth and PHA production
(results are provided at 48 h of fermentation, without fortification of extra carbon source and minerals)

| Initial SS concentration (g/L) | Unwashed sludge | | | Washed sludge | | |
|---|---|---|---|---|---|---|
| | Final SS concentration (g/L) | CFU/mL | PHA content (% w/w) | Final SS concentration (g/L) | CFU/mL | PHA content (% w/w) |
| 10 | 6.9 | 4.90E+09 | 4.23 | 5.9 | 5.40E+10 | 4.6 |
| 15 | 11.3 | 4.40E+09 | 7.75 | 12.1 | 5.80E+10 | 11.46 |
| 20 | 15.66 | 5.10E+09 | 9.92 | 15.8 | 7.90E+10 | 10.92 |
| 25 | 22.27 | 5.60E+09 | 9 | 18.1 | 6.90E+10 | 7.31 |

Alkali (sodium hydroxide) dose for pre-treatment of sludge: The goal of the pre-treatment process is fractionating the main components of the lignocellulose materials, to dissolve the maximum sludge solids and cell lysis, which leads to release of nutrients that can be utilized by growing microorganism. Therefore, in this experiment, 10 and 30 g/L suspended solids concentration was used and treated with different dose of sodium hydroxide (0.05, 0.07, 0.09, 0.11, 0.13 g of NaOH/g of suspended solids). Thereafter, the sludge was sterilized at 121° C. for 30 min. The suspended solids concentration was measured for each flask by taking 10 mL of samples. The dose of sodium hydroxide, at which maximum sludge solids were dissolved was selected for further experiments.

The maximum sludge hydrolysis for 10 g/L (after treatment, final SS conc.-4.1 g/L) and 30 g/L (after treatment final SS conc.-11.3 g/L) of SS was obtained at 0.13 g of NaOH/g of SS.

Suspended solids concentration for PHA production: Various inhibitors such as aliphatic adds, phenolics and furan derivatives could be released during the sodium hydroxide treatment, which can inhibit the growth of microorganisms and accumulation of PHA. The inhibitors can be increased with increasing concentration of suspended solids, because at higher SS, larger amount of inhibitors will be released during the pre-treatment with sodium hydroxide, which can directly affect the growth as well as accumulation of PHA. Therefore, pre-treatment of varying SS (10, 15, 20, 25, 30 g/L) concentration was performed with a NaOH concentration of 0.133 g NaOH/g SS. After sterilization of sludge at 121° C. for 30 min., pretreated suspended solids were allowed to come at room temperature and under sterile conditions, pH was adjusted to 6.8 using 4 N $H_2SO_4$. All shake flasks were inoculated with 2-10% (v/v) of pre-culture-2, which was prepared in the same way as production media (various SS concentration, no supplementation of extra carbon and minerals). The flasks were kept for incubation at 30° C., 150 rpm for 96 h and samples were analyzed for suspended solids concentration, CFU (colony forming unit) and PHA concentration.

After alkaline treatment (0.133 g NaOH/g of SS) of washed sludge with varying SS concentration, suspended solids concentration decreased from 15, 20, 25 and 30 g/L to 4.7, 5.0, 8.0 and 13 g/L, respectively. The PHA content of biomass (9.67% w/w) was maximum using SS concentration of 15 g/L at 24 h. However, the obtained PHA content (9.67% w/w) was lower as compared to that obtained by using only heat-treated washed sludge (11.46% w/w) at same SS concentration. The lower PHA accumulation using alkaline treatment could be due to formation of toxic components during hydrolysis.

Example 3

The toxic materials released during sludge hydrolysis using sodium hydroxide were found to inhibit PHA accumulation Lime or calcium hydroxide treatment was used in order to reduce the inhibitory components generated during sludge hydrolysis.

Different doses of calcium hydroxide (0.05, 0.07, 0.09, 0.11, 0.13 g of $Ca(OH)_2$/g of suspended solids) were added to a 15 g/L SS concentration of washed sludge into different flasks. After sterilization of sludge, glucose (20 g/L), ammonium chloride (1 g/L) and minerals were supplemented (composition same as Example 1) in each flasks. The pH was adjusted to 6.8 using 4N sulfuric acid and inoculation was done by using 2-10% (v/v) of pre-culture-2 (composition same as production media and pre-culture will be grown for 24 h), thereafter incubation was done at 30° C., 150 rpm for 96 h. The samples were withdrawn after every 24 h for biomass concentration (g/L), reducing sugars consumption (g/L), CFU and PHA concentration (g/L).

The 0.11 g of calcium hydroxide/g of SS was found to allow for maximum cell growth and PHA accumulation. The PHA concentration was increased from 1.10 g/L (using NaOH treated sludge) to 4.45 g/L using calcium hydroxide detoxification in shake flasks. Other calcium hydroxide concentrations also yielded high cell growth and PHA accumulation, as can be seen in Table 3 below, compared to the NaOH control.

TABLE 3

Washed (Conditioned) sludge pre-treatment with different dose of calcium hydroxide (for detoxification) and production of PHA in the pre-treated sludge (with fortification of extra carbon source and minerals)

| Washed sludge SS-15 g/L | CFU/mL) | SS (g/L) | PHA (%) | PHA (g/L) |
|---|---|---|---|---|
| Control (No sludge, synthetic media using glucose) | 9.10E+11 | 2.95 | 46.72 | 1.38 |
| Control - NaOH (0.133 g/g of SS) treated washed sludge | 9.60E+12 | 10.9 | 8.91 | 0.97 |

TABLE 3-continued

Washed (Conditioned) sludge pre-treatment with different dose of calcium hydroxide (for detoxification) and production of PHA in the pre-treated sludge (with fortification of extra carbon source and minerals)

| Washed sludge SS-15 g/L | CFU/mL) | SS (g/L) | PHA (%) | PHA (g/L) |
|---|---|---|---|---|
| Ca(OH)$_2$ (0.09 g/g of SS) treated washed sludge | 8.00E+12 | 15.32 | 17.42 | 2.67 |
| Ca(OH)$_2$ (0.11 g/g of SS) treated washed sludge | 7.80E+12 | 15.45 | 30.82 | 4.76 |
| Ca(OH)$_2$ (0.13 g/g of SS) treated washed sludge | 7.40E+12 | 14.99 | 20.44 | 3.06 |
| Ca(OH)$_2$ (0.15 g/g of SS) treated washed sludge | 5.80E+11 | 14.56 | 15.91 | 2.32 |

Example 4

Experiments were conducted to produce FHA using sludge fortified with glucose as an extra carbon source and treated with calcium hydroxide prior to sterilization (fed batch fermentation).

Fed batch fermentation was performed in 5 L or 7 L fermenters to verify the stability and consistency of PHA accumulation using pulp and paper activated sludge (PPAS) with a pure bacterial culture. Glucose (pure carbon substrate) was used as an additional carbon substrate in order to increase PHA accumulation.

A suspended solids concentration of 15 g/L from shake flasks experiment was used in this study and a concentration of calcium hydroxide of 0.11 g Ca(OH)$_2$/g of SS was added into the washed sludge before sterilization. After sterilization of sludge, media was supplemented with sterilized glucose and minerals under aseptic conditions. The temperature was maintained at 30° C. by circulating water through the jacket. Fermentation pH was controlled automatically at 6.8±0.1 through computer-controlled peristaltic pumps by using 4N sulfuric acid and 4N NaOH. Both DO and pH were continuously monitored by means of a polarographic dissolved oxygen probe and pH sensor (Mettler-Toledo, USA), respectively.

Pre-culture-2 (composition same as production media except low SS (10 g/l) and glucose (10 g/L) concentration was used) cultivated at 30° C., 150 rpm for 24 h was transferred to the sludge production media. The same concentration of nitrogen and minerals was supplemented for 0, 12 and 24 h, while after 24 h, low concentration of minerals and nitrogen was supplemented throughout the fermentation (Five feeds at 36, 42, 60, 72 and 84 h). Composition of sludge production media and feed solution is given in Table 4. The feeding of glucose was done based upon the consumption throughout the fermentation.

TABLE 4

Composition of production media and feed solution for fermenter

| | Concentration (g/L) | | |
|---|---|---|---|
| Component | Production media (0 h) | Feed solution 1 (Fed at 12 and 24 h) | Feed solution 2 (Fed at 24, 36, 48, 60, 72, 84 h) |
| Conditioned and Ca(OH)$_2$ treated sludge (g/L) | 15 | — | — |
| Glucose or Crude glycerol solution (carbon equivalent)-g/L | 20.0 | 10.0 | 10.0 |
| NH$_4$Cl (g/L) | 1.00 | 1.00 | 0.20 |
| Na$_2$HPO$_4$•12H$_2$O (g/L) | 6.00 | 6.00 | 0.50 |
| KH$_2$PO$_4$ (g/L) | 2.40 | 2.40 | 0.20 |
| MgSO$_4$•7H$_2$O (g/L) | 0.50 | 0.50 | 0.04 |

Conditioned and Ca(OH)$_2$ treated sterilized sludge (SS concentration –15 g/L) gave a maximum PHA content of 86.5% (w/w), biomass concentration of 51.97 g/L and PHA concentration of 44.97 g/L (as seen on FIG. 6). The same experiment was repeated by using PPMAS collected at different time period and results were reproducible, which addresses a typical problem of inconsistency or variability in PHA accumulation in techniques of the prior art.

Moreover, high PHA yield of 0.60 g of PHA/g of glucose consumed (1.5 g of PHA/g of carbon consumed) was achieved using sludge fortified with glucose. However tow PHA yield of 0.36 g/g of glucose consumed (0.9 g of PHA/g of carbon consumed) was achieved using only glucose as a substrate without addition of sludge (Table 5).

TABLE 5

Comparison of PHA yield for sludge fortified with glucose and only glucose as a substrate

| Substrate | SS (g/L) | PHA % (w/w) | PHA (g/L) | Total Glucose consumed (g/L) | Total carbon consumed (g/L) | Global PHA yield(g of of PHA/g of glucose Consumed) | Global PHA yield(g of of PHA/g of carbon Consumed) | Reference |
|---|---|---|---|---|---|---|---|---|
| Glucose | 31.5 | 89.1 | 28.07 | 77 | 30.8 | 0.36 | 0.91 | The present application |
| Glucose + sludge (Initial SS-15 g/L) | 51.9 | 86.5 | 44.97 | 75 | 30 | 0.60 | 1.50 | The present application |
| Glucose | | | | | | 0.32 | 0.8 | Nonato et al. 2001; |

TABLE 5-continued

Comparison of PHA yield for sludge fortified with glucose and only glucose as a substrate

| Substrate | SS (g/L) | PHA % (w/w) | PHA (g/L) | Total Glucose consumed (g/L) | Total carbon consumed (g/L) | Global PHA yield(g of of PHA/g of glucose Consumed) | Global PHA yield(g of of PHA/g of carbon Consumed) | Reference |
|---|---|---|---|---|---|---|---|---|
| | | | | | | | | Mozumder et al., 2014 |

Example 5

Experiments were conducted to produce PHA using sludge fortified with high soap containing crude glycerol (composition in Table 6) as an extra carbon source and treated with calcium hydroxide prior to sterilization.

TABLE 6

Crude glycerol solution characterization

| Test | Crude glycerol solution |
|---|---|
| pH | 9.36 |
| Density | 5.2 g/5 mL or 1.04 g/mL |
| Methanol content | 30% w/v |
| Water content | 30.43% w/v |
| Catalyst | 0.66% w/v |
| Glycerol concentration | 160 g/L or (16% w/v) |
| Soap content | 280 g/L (or) (28% w/v) |

Unconditioned (Unwashed) and conditioned (washed) sludge with SS concentration of 15 g/L was used m two different fermenters. A concentration of 0.11 g $Ca(OH)_2$/g of SS was added into the sludge (collected from white birch pulp and paper industry, Quebec city, Canada) before sterilization. After sterilization of sludge, media was supplemented with sterilized crude glycerol solution (8 g carbon/L) and minerals under aseptic conditions.

Pre-culture-2 (composition same as production media except low SS (10 g/L) and crude glycerol (4 g carbon/L) concentration was used) cultivated at 30° C., 150 rpm for 24 h was transferred to the sludge production media. The same concentration of nitrogen and minerals was supplemented for 0, 12 and 24 h, while after 24 h, low concentration of minerals and nitrogen was supplemented throughout the fermentation (five feeds at 36, 42, 60, 72 and 84 h). Composition of sludge production media and feed solution is given in Table 4. The feeding of crude glycerol solution was done based upon the consumption of glycerol and soap throughout the fermentation.

The maximum biomass concentration of 41.2 g/L was achieved with PHA content of 72.1% (w/w) and PHA concentration of 29.7 g/L using conditioned sludge with initial SS of 15 g/L (as seen on FIG. 7). However, biomass concentration of 38.9 g/L was achieved with PHA content of 55.7% (w/w) and PHA concentration of 21.9 g/L using unconditioned sludge with initial SS of 15 g/L (as seen on FIG. 8). These results show that sludge washing has an effect on PHA accumulation as PHA content and PHA concentration were increased by 17% and 8 g/L respectively after elimination of toxic compounds during sludge washing.

The high PHA yield of 0.98 g of PHA/g of carbon consumed (both soap and glycerol) was achieved in the experiment using conditioned sludge fortified with crude glycerol. However, low PHA yield of 0.73 g of PHA/g of carbon consumed (both soap and glycerol) was achieved in the experiment using only crude glycerol as a substrate without addition of sludge (Table 7)

TABLE 7

Comparison of PHA yield for sludge fortified with crude glycerol and only crude glycerol as a substrate

| Substrate | SS(g/L) | PHA % (w/w) | PHA (g/L) | Total Substrate consumed (glycerol + soap g/L) | Total carbon consumed (g/L) | Global PHA yield (g of PHA/g of carbon Consumed) | Reference |
|---|---|---|---|---|---|---|---|
| Crude glycerol | 30.7 | 75.7 | 23.24 | 58.3 | 31.99 | 0.73 | The present application |
| Crude glycerol + Sludge (Initial SS-15 g/L) | 41.2 | 72.1 | 29.71 | 55.5 | 30.44 | 0.98 | The present application |
| Crude glycerol | | | | | | 0.56 | Paula et al., 2017 |

Example 6

Experiments were conducted to produce PHA using a sludge having a higher SS concentration and treated with calcium hydroxide prior to sterilization.

A conditioned sludge with high SS concentration of 25 g/L was used and a concentration of calcium hydroxide of 0.11 g $Ca(OH)_2$/g of SS was added into the sludge before sterilization. After sterilization of sludge, media was supplemented with sterilized crude glycerol solution (8 g carbon/L, composition in Table 6) and minerals under aseptic conditions.

Pre-culture-2 (composition same as production media except low SS (10 g/L) and crude glycerol (4 g carbon/L) concentration was used) cultivated at 30° C., 150 rpm for 24 h was transferred to the sludge production media. The same concentration of nitrogen and minerals was supplemented for 0, 12 and 24 h, while after 24 h, low concentration of minerals and nitrogen was supplemented throughout the fermentation (five feeds at 36; 42, 60, 72 and 84 h) Composition of sludge production media and feed solution is given in Table 4. The feeding of crude glycerol solution was done based upon the consumption throughout the fermentation.

The conditioned sludge with high concentration of solids gave a biomass concentration of 48.7 g/L, a PHA content of 68% (w/w) and PHA concentration of 33.2 g/L with a PHA yield of 0.86 g of PHA/g of carbon consumed (both soap and glycerol) was obtained (As seen on FIG. 9).

The biomass and PHA concentration were higher using initial SS concentration of 25 g/L as compared to that achieved by using lower SS concentration (15 g/L) Use of high solids concentration in the fermentation process can ultimately decrease the volume of the fermenter required to process a given amount of sludge generated by a specific plant. This in turn reduces the establishment cost of a PHA

Example 7

Experiments were conducted to produce PHA using conditioned sludge fortified with acetic acid as an extra carbon source and treated with calcium hydroxide prior to sterilization.

Acetic acid was also studied as an additional carbon substrate along with sludge using a pH stat fed batch strategy. Whenever the pH of broth inside the fermenter increased from 6.8 to 6.85 (variation of pH 0.05), acetic acid was automatically fed into the fermenter by add pump. The pre-culture 2 for all the experiments with acetic acid was prepared by using crude glycerol solution. The conditioned pulp and paper sludge with SS concentration of 25 g/L was used and a concentration of calcium hydroxide of 0.11 g $Ca(OH)_2$/g of SS was added into the sludge before sterilization. After sterilization of sludge, media was supplemented with minerals under aseptic conditions. Pre-culture-2 (composition same as production media except low SS (10 g/L) and crude glycerol (4 g carbon/L) (Composition given in Table 6) concentration was used) cultivated at 30° C., 150 rpm for 24 h was transferred to the sludge production media. The same concentration of nitrogen and minerals was supplemented at 0, 12 and 24 h, while after 24 h, low concentration of minerals and nitrogen was supplemented throughout the fermentation (five feeds at 36, 42.60, 72 and 84 h). Acetic acid was automatically added in the fermenter on the basis of pH based fed batch strategy.

The maximum biomass concentration of 44.7 g/L was achieved with PHA content of 68% (w/w) and PHA concentration of 30.5 g/L using conditioned sludge of initial SS 25 g/L (As seen on FIG. 10). High PHA yield of 0.60 g of PHA/g of acetic acid consumed (1.5 g of PHA/g of carbon consumed) was achieved by using conditioned sludge and acetic acid as an additional carbon substrate.

The comparatively low PHA yield of 0.2 g of PHA/g of mixture of carbon substrate (acetic acid, butyric acid, succinic acid and propionic acids) consumed was reported by Chakraborty et al., 2012. In the other study by Yu et al., (2002), the average PHA yield of 0.39 g of PHA/g of mixture of carbon substrate (acetic acid, butyric acid and propionic acids) consumed was reported.

Example 8

Experiments were conducted using unconditioned sludge collected from different pulp and paper industries.

The composition of sludge changes from one plant to another. In this series of experiments, pulp and paper sludge was collected from different pulp and paper industries such as Alma and Dolbeau. It is being considered that the sludge varies with time and nature of the process used inside the industry. Moreover, in wastewater, the sludge microbial communities are sensitive to changes in the process stream like organic feed load, chemical addition, change in SRT, HRT, temperatures, pH of operation etc., thereby changing the PHA content. It can be also hypothesized that sludge composition will be varied from one industry to another. Therefore, in this section, the established method was used for PHA production using pulp and paper sludge collected from different industries in order to check the sustainability of the process.

A concentration of calcium hydroxide of 0.11 g of $Ca(OH)_2$/g of SS was added into the unwashed Alma and Dolbeau sludge before sterilization in different experiments. After sterilization of sludge, media was supplemented with sterilized crude glycerol solution (8 g carbon/L) (composition given in Table 6) and minerals under aseptic conditions.

Pre-culture-2 (composition same as production media except low SS (10 g/l) and crude glycerol (4 g carbon/L) (composition given in Table 6) concentration was used) cultivated at 30° C., 150 rpm for 24 h was transferred to the sludge production media. The same concentration of nitrogen and minerals was supplemented for 0, 12 and 24 h. while after 24 h, low concentration of minerals and nitrogen was supplemented throughout the fermentation (five feeds of crude glycerol at 36, 42, 60, 72 and 84 h). Composition of sludge production media and feed solution is given in Table 4. The feeding of crude glycerol solution was done based upon the consumption of soap and glycerol throughout the fermentation.

Alma unwashed sludge with initial SS concentration of 15 g/L and crude glycerol solution as an additional carbon substrate gave maximum biomass concentration of 40.12 g/L and biomass PHA content of 53.45% (w/w) and PHA concentration of 21.44 g/L. In a similar experimental study under similar conditions of fermentation process of Dolbeau unwashed sludge, the maximum biomass concentration of 41.32 g/L was achieved with PHA content of 55.2% (w/W) and PHA concentration of 22.8 g/L. These results were similar to that obtained by using unwashed sludge of White birch pulp aid paper industry under similar conditions of fermentation. It is evident from the results obtained by using sludge collected from three different pulp and paper industries wastewater treatment plant that the composition of sludge does not affect the PHA production using pure culture process, which was major bottleneck with the PHA production using mixed culture.

Example 9

Experiments were conducted to produce PHA using a large scale 150 L fermenter.

PHA production was also performed at 150 L (total volume) fermenter with unconditioned sludge (without decantation) obtained from Dolbeau and crude glycerol as an additional carbon substrate to confirm the consistency of the developed process.

Pre-culture-2 (composition same as production media except low SS (10 g/L) and crude glycerol (4 g carbon/L) concentration was used) cultivated at 30° C., 150 rpm for 24 h was transferred to the pre-culture 3 (composition same as production media except low SS (10 g/L) and crude glycerol (4 g carbon/L concentration was used, composition given in Table 6) and cultivation conditions were same as pre-culture 2. After 24 h, the pre-culture 3 was transferred to 150 L fermenter with working volume 100 L. The nitrogen and minerals were supplemented for 0, 12 and 24 h, while after 24 h, low concentration of minerals and nitrogen was supplemented throughout the fermentation (five feeds at 36, 42, 60, 72 and 84 h). Composition of sludge production media and feed solution is given in table 4. The feeding of crude glycerol solution was done based upon the consumption of soap and glycerol throughout the fermentation.

The maximum biomass concentration of 40 g/L was achieved with PHA content of 54% (w/w) and PHA concentration of 21.5 g/L using unconditioned sludge with initial SS of 15 g/L. These results were similar to the experiment performed by using 5 L fermenter with unconditioned sludge of 15 g/L, which shows the consistency of the new PHA production process at different scale.

It was shown that sludge is a substrate that can be used for pure culture, alone or in combination with other waste substrates (like crude glycerol etc.). The process can address at least in part the issue of inconsistency of PHA concentration, lower PHA content and lower PHA yield attained during PHA production using mixed microbial culture. Moreover, less chemical treatment is required for further extraction and purification of PHA due to the high concentration of PHA in the biomass produced during fermentation.

Example 10

Experiments were conducted at 5 L fermenter to further enhance biomass concentration, PHA concentration and PHA yield by using conditioned sludge fortified with high soap containing crude glycerol (composition in Table 6) as an extra carbon source and treated with calcium hydroxide prior to sterilization. The continuous carbon fed batch strategy was used to maintain the optimum carbon concentration (8±1 g carbon of crude glycerol solution/L of medium) for microorganism throughout the fermentation.

For 5 L fermenter, Pre-culture-2 (composition same as production media except low SS (10 g/L) and crude glycerol (4 g carbon/L) concentration was used) cultivated at 30° C., 150 rpm for 24 h was transferred to the sludge production media.

The same concentration of nitrogen and minerals was supplemented for 0, 12 and 24 h, while after 24 h, low concentration of minerals and nitrogen was supplemented throughout the fermentation (five feeds at 36, 42, 60, 72 and 84 h). Composition of sludge production media and feed solution is given in Table 8.

TABLE 8

Composition of production media and feed solution for fermenter with continuous fed batch fermentation strategy

| | Concentration (g/L) | | |
|---|---|---|---|
| Component | Production media (0 h) | Feed solution 1 (Fed at 12 and 24 h) | Feed solution 2 (Fed at 24, 36, 48, 60, 72, 84 h) |
| Conditioned and Ca(OH)$_2$ treated sludge (g/L) | 15 | — | — |
| Crude glycerol solution (carbon equivalent)-g/L | 20.0 | Continuous mode to maintain optimum carbon concentration of 8 g carbon/L in fermenter | |
| NH$_4$Cl (g/L) | 1.00 | 1.00 | 0.20 |
| Na$_2$HPO$_4$·12H$_2$O (g/L) | 6.00 | 6.00 | 0.50 |
| KH$_2$PO$_4$ (g/L) | 2.40 | 2.40 | 0.20 |
| MgSO$_4$·7H$_2$O (g/L) | 0.50 | 0.50 | 0.04 |

During fed batch fermentation, crude glycerol solution was added intermittently, based upon consumption of glycerol and soap. However, continuous fed batch strategy can alternatively be used to provide an optimum carbon concentration (8 g carbon/l) for microorganism which is maintained in the medium throughout the fermentation. The continuous fed batch strategy can also help to maintain the C/N ratio throughout the fermentation.

Therefore, at 0 h, the crude glycerol solution (carbon equivalent equal to 20 g carbon/L of glycerol or 8 g carbon/L) was added to the medium. Thereafter, crude glycerol solution was automatically added (by adjusting flow rate of peristaltic pump to add the required amount of crude glycerol solution as optimized during intermittent fed batch strategy). During intermittent fed-batch strategy, the carbon was added based upon the consumption and bacteria required 4 g C of crude glycerol solution/L of medium in every 12 h. Therefore, in the continuous fed batch strategy, the same amount of carbon was added slowly into the fermenter by adjusting flow rate of the peristaltic pump during a time period of 12 h. Thus, it was observed that same carbon concentration was maintained throughout the fermentation.

Thus, the use of a continuous carbon fed batch fermentation strategy with Ca(OH)$_2$ boated PPMAS as a substrate and crude glycerol as an additional carbon substrate led to a biomass concentration of 58 g/L with 42 g/L of PHA concentration, as compared to 41.2 g/L of biomass concentration and 29.7 g/L of PHA concentration obtained with intermittent carbon fed batch strategy. In addition, the use of a continuous carbon fed batch fermentation strategy led to a PHA yield of 1.17 g of PHA/g of carbon consumed, as compared to a PHA yield of 0.98 g of PHA/g of carbon consumed obtained with intermittent carbon fed batch strategy (Table 9).

TABLE 9

Comparison of PHA yield for intermittent carbon fed batch
and continuous carbon fed batch fermentation strategy

| Substrate | SS (g/L) | PHA % (w/w) | PHA (g/L) | Total Substrate consumed (glycerol + soap g/L) | Total carbon consumed (g/L) | Global PHA yield (g of PHA/g of carbon Consumed) | Reference |
|---|---|---|---|---|---|---|---|
| Crude glycerol | 30.7 | 75.7 | 23.24 | 58.3 | 31.99 | 0.73 | The present application |
| Intermittent fed batch strategy (Crude glycerol + Sludge (Initial SS-15 g/L) | 41.2 | 72.1 | 29.71 | 55.5 | 30.44 | 0.98 | The present application |
| Continuous fed batch strategy (Crude glycerol + Sludge (Initial SS-15 g/L) | 58 | 72.4 | 42 | 60.6 | 35.80 | 1.17 | The present application |

Example 11

Experiments were conducted to produce PHA using a large scale 150 L fermenter. PHA production was also performed at 150 L (total volume) fermenter for continuous fed batch strategy with conditioned sludge obtained from Dolbeau and crude glycerol as an additional carbon substrate (secondary carbon source) to confirm the consistency of the developed process.

Pre-culture-2 (which composition is the same as production media except low SS (10 g/L) and crude glycerol (4 g carbon/L) concentration was used) cultivated at 30° C., 150 rpm for 24 h, was transferred to the pre-culture 3 (which composition is the same as production media except low SS (10 g/L) and crude glycerol (4 g carbon/L concentration was used, composition given in Table 6) and cultivation conditions were same as pre-culture 2. After 24 h. the pre-culture 3 was transferred to 150 L fermenter with a working volume of 100 L. The nitrogen and minerals were supplemented for 0, 12 and 24 h, while after 24 h. low concentration of minerals and nitrogen was supplemented throughout the fermentation (five feeds at 36, 42, 60, 72 and 84 h). Composition of sludge production media and feed solution is given in Table 8.

In continuous carbon fed batch fermentation strategy as discussed in example 10, the same concentration of carbon was added slowly into the fermenter. The crude glycerol solution was sterilized at 121° C. for 15 min in autoclave and cooled down to room temperature. Under sterile conditions, the crude glycerol solution was transferred to a sterile feed plastic tank in laminar air flow. Thereafter, the sterile feed plastic tank (carbon feed tank) was connected to a fermenter. Due to the fact that crude glycerol solution consists of soap and glycerol, which are immiscible together, the carbon feed tank was placed on magnetic stirrer in order to mix crude glycerol solution continuously. The feed flow rate of crude glycerol solution to fermenter was manually set up by setting frequency of rotation of a peristaltic pump to 5 rpm (on for every 17 sec on and off for 60 sec). Accordingly, the optimum carbon concentration (8±1 g carbon/L) was maintained in fermentation medium (culture medium) based upon consumption (sample was analyzed for glycerol and soap concentration, each 6 h) and considering the increased volume of the fermentation broth inside the fermenter with time. The volume of crude glycerol solution added inside the fermenter was thereby increased (interval time (on) was increased up to 20 sec).

The maximum biomass concentration of 58.4 g/L was achieved with biomass PHA content of 70% (w/w) and PHA concentration of 40 g/L using conditioned sludge with initial SS of 15 g/L with continuous fed batch fermentation strategy at 150 L fermenter. These results were similar to the experiment performed by using 5 L fermenter with conditioned sludge of 15 g/L, which shows the consistency of the PHA production process at different scale.

The invention claimed is:

1. A process for producing polyhydroxyalkanoates (PHA), comprising:
   providing a treated waste stream consisting of a secondary sludge comprising suspended solids;
   treating the waste stream to produce a treated waste stream, the treating comprising:
   adding a calcium-containing mineral to said waste stream in an amount between 0.05 grams and 0.5 grams per gram of suspended solids; and
   heat-treating the waste stream in the presence of the calcium-containing mineral, to sterilize the waste stream;
   forming a culture medium comprising the heated waste stream as a carbon source;
   adding at least one strain of PHA-producing microorganism to the culture medium;
   adding a secondary carbon source to the culture medium;
   subjecting the culture medium to fermentation to initiate PHA production by the PHA-producing microorganisms using the carbon source and the secondary carbon source to produce a fermentation mixture comprising the PHA that is accumulated in the PHA-producing microorganisms; and
   subjecting the fermentation mixture to cell disruption to allow the PHA to be extracted from the PHA-microorganisms to form an extraction mixture comprising extracted PHA and cellular material;
   wherein the calcium-containing mineral is added to the waste stream prior to and/or during the heat-treating of the waste stream;
   wherein at least one strain of the PHA-producing microorganisms is added to the culture medium prior to and/or during the fermentation; and wherein the secondary carbon source is added to the culture medium prior to and/or during the fermentation.

2. The process of claim 1, wherein the waste stream is a pulp and paper activated sludge stream.

3. The process of claim 1, wherein the calcium-containing mineral comprises at least one of calcium carbonate, calcium hydroxide and calcium oxide.

4. The process of claim 1, further comprising filtering the waste stream to remove coarse fibers, prior to adding the calcium-containing mineral to the waste stream, thereby obtaining a waste stream-filtrate.

5. The process of claim 4, further comprising settling the waste stream filtrate to decant unfiltered solids, prior to adding the calcium-containing mineral to the waste stream, thereby obtaining a decanted waste stream.

6. The process of claim 5; further comprising, prior to adding the calcium-containing mineral to the waste stream, washing the decanted waste stream to obtain washed solids.

7. The process of claim 6, wherein washing the decanted waste stream comprises:
centrifuging the decanted waste stream to obtain centrifuged solids.

8. The process of claim 7, further comprising re-suspending the centrifuged solids in an aqueous medium, to obtain a suspension; and
re-centrifuging the suspension to obtain the centrifuged solids.

9. The process of claim 1, further comprising, prior to adding the calcium-containing mineral to the waste stream:
adjusting a suspended solids (SS) concentration in the waste stream to a pre-determined concentration between 5 grams per liter and 50 grams per liter, to obtain a conditioned waste stream; and
adding the calcium-containing mineral to the conditioned waste stream, wherein heat-treating the waste stream comprises heat-treating the conditioned waste stream.

10. The process of claim 9; wherein adjusting the SS concentration is performed on the washed solids.

11. The process of claim 9, wherein the pre-determined concentration is between 10 grams per liter and 20 grams per liter.

12. The process of claim 1, wherein the secondary carbon source comprises a carboxylic acid, a saccharide, an oil, an alcohol or a combination thereof.

13. The process of claim 1, wherein the fermentation step comprises maintaining the pH of the culture medium between 6, 5 and 7, 5 and/or maintaining the temperature between 25° C. and 35° C.

14. The process of claim 1, wherein the least one strain of PHA-producing microorganism is a single strain of PHA-producing microorganism.

15. The process of claim 1, wherein the at least one strain of PHA-producing microorganism is selected from the group consisting or *Bacillus megaterium, Comamonas testosteroni, Cupriavidus necator* 11599, *Cupriavidus necator* H16, *Pseudomonas guezennei* biovar, *Tikehau, R. eutropha, E. coli*, engineered *E. coli, Alcaligenes latus, Sphingobacterium* sp. ATM, *Plasticicumulans acidivorans, Bacillus tequilensis, Haloferax mediterranei, H. mediterranei, Pseudomonas fluorescens* A2a5 and *Ralstonia eutropha* H16.

16. The process of claim 1, wherein subjecting the fermentation mixture to cell disruption comprises heat-treating the fermentation mixture so as to lyse at least a portion of the PHA-producing microorganisms, thereby releasing the PHA.

17. The process of claim 16, wherein heat-treating the fermentation mixture is performed at a temperature between 80° C. and 125° C.

18. The process of claim 1, further comprising drying the extraction mixture comprising the PHA.

19. The process of claim 1, comprising maintaining a carbon concentration in the culture medium at an optimum carbon concentration based on a carbon consumption of the PHA-producing microorganism during the fermentation.

20. The process of claim 1, wherein the calcium-containing mineral comprises calcium hydroxide.

\* \* \* \* \*